(12) United States Patent
Alam et al.

(10) Patent No.: US 12,295,696 B2
(45) Date of Patent: May 13, 2025

(54) PASSIVE ASSISTIVE ALERTS USING ARTIFICIAL INTELLIGENCE ASSISTANTS

(71) Applicant: MatrixCare, Inc., Bloomington, MN (US)

(72) Inventors: Samia Sadeque Alam, Houston, TX (US); Keegan Duane Dsouza, Ocala, FL (US); Kedar Mangesh Kadam, Nova Scotia (CA); Amy Ostrem, Maple Grove, MN (US); Adhiraj Ganpat Prajapati, St. Paul, MN (US)

(73) Assignee: MatrixCare, Inc., Bloomington, MN (US)

( * ) Notice: Subject to any disclaimer, the term of this patent is extended or adjusted under 35 U.S.C. 154(b) by 129 days.

(21) Appl. No.: 18/064,111

(22) Filed: Dec. 9, 2022

(65) Prior Publication Data

US 2023/0210372 A1 Jul. 6, 2023

Related U.S. Application Data

(60) Provisional application No. 63/295,369, filed on Dec. 30, 2021.

(51) Int. Cl.
| | |
|---|---|
| *A61B 5/22* | (2006.01) |
| *A61B 5/00* | (2006.01) |
| *G06V 40/16* | (2022.01) |
| *G10L 25/30* | (2013.01) |
| *G10L 25/66* | (2013.01) |
| *G06V 20/68* | (2022.01) |

(52) U.S. Cl.
CPC ............ *A61B 5/0022* (2013.01); *A61B 5/002* (2013.01); *A61B 5/4803* (2013.01); *A61B 5/7264* (2013.01); *A61B 5/746* (2013.01); *G06V 40/174* (2022.01); *G10L 25/30* (2013.01); *G10L 25/66* (2013.01); *G06V 20/68* (2022.01)

(58) Field of Classification Search
CPC ..... A61B 5/0022; A61B 5/002; A61B 5/4803; A61B 5/7264; A61B 5/746; G06V 40/174; G06V 20/68; G10L 25/30; G10L 25/66
USPC .................................................... 340/286.07
See application file for complete search history.

(56) References Cited

U.S. PATENT DOCUMENTS

| | | | |
|---|---|---|---|
| 2012/0330109 A1* | 12/2012 | Tran ................... | A61B 5/14532 600/509 |
| 2013/0176125 A1* | 7/2013 | Beck ...................... | G16H 40/67 340/573.1 |
| 2015/0022343 A1* | 1/2015 | Sanders ............... | A61B 5/4806 340/521 |

(Continued)

*Primary Examiner* — Zhen Y Wu
(74) *Attorney, Agent, or Firm* — Patterson + Sheridan, LLP

(57) ABSTRACT

Embodiments herein determine when to place a passive assistive call using personal artificial intelligence (AI) assistants. The present embodiments improve upon the base functionalities of the assistant devices by monitoring the usually discarded or filtered-out environmental sounds to identify when a person is in distress to automatically issue an assistive call in addition to or alternatively to monitoring user speech for active commands to place assistive calls. The assistant device may be in communication with various other sensors to enhance or supplement the audio assessment of the persons in the environment, and may be used in a variety of scenarios where prior call systems struggled to quickly and accurately identify distress in various monitored persons (e.g., patients) including falls, stroke onset, and choking.

15 Claims, 12 Drawing Sheets

(56) References Cited

U.S. PATENT DOCUMENTS

| | | | |
|---|---|---|---|
| 2016/0163168 A1* | 6/2016 | Brav | G08B 29/188 |
| | | | 381/56 |
| 2016/0192848 A1* | 7/2016 | Ravishankar | G16H 50/20 |
| | | | 340/573.1 |
| 2017/0270820 A1* | 9/2017 | Ashby | A61B 5/7465 |
| 2019/0108841 A1* | 4/2019 | Vergyri | A61B 5/7282 |
| 2019/0279480 A1* | 9/2019 | Lee | A61B 5/1121 |
| 2020/0288294 A1* | 9/2020 | Yang | H04W 4/90 |
| 2020/0360652 A1* | 11/2020 | Kanana | A61B 5/7455 |
| 2020/0394887 A1* | 12/2020 | Heath | G08B 21/0469 |
| 2021/0052198 A1* | 2/2021 | Parvaneh | A61B 5/1117 |
| 2021/0244377 A1* | 8/2021 | Amoh | A61B 5/7257 |
| 2022/0000375 A1* | 1/2022 | Meisal | A61B 5/28 |
| 2022/0166851 A1* | 5/2022 | Fong | G16Y 20/20 |
| 2022/0286833 A1* | 9/2022 | Khalid | H04W 4/70 |

\* cited by examiner

PASSIVE ASSISTIVE ALERTS USING ARTIFICIAL INTELLIGENCE ASSISTANTS

CROSS-REFERENCE TO RELATED APPLICATIONS

This application claims benefit of U.S. provisional patent application Ser. No. 63/295,369 filed Dec. 30, 2021. The aforementioned related patent application is herein incorporated by reference in its entirety.

INTRODUCTION

Embodiments of the present disclosure relate to audio recognition including natural language processing. More particularly, a personal artificial intelligence assistant is used to detect abnormal or non-responsive speech patterns and other indicative audio cues to determine when a person is in distress and automatically call for assistance on behalf of that person.

Various technologies exist that allow for a person to call for assistance when in distress, but require the person to activate a call response (e.g., press one or more buttons) or rely on vital sign monitoring (e.g., an electrocardiogram) to trigger a call-worthy condition before assistance is requested. However, persons may require assistance when they are incapacitated or otherwise unable to activate a call response or when they present various vital signs in a healthy range that would not trigger a call-worthy condition. These technologies are also often intrusive or embarrassing to have ready for use, and the persons who need them the most may forgo keeping these technologies at the ready out of embarrassment or due to the intrusiveness of these technologies. Accordingly, various vulnerable persons need non-intrusive technologies that allow for passive assistance.

SUMMARY

Certain embodiments provide a method that includes capturing, via an Artificial Intelligence (AI) assistant device, audio from an environment, filtering, via a machine learning model provided by the AI assistant device, an environmental sound from utterances in the audio, determining, via an audio recognition engine provided by the AI assistant device and based on the environmental sound, that a patient is in distress and is non-responsive, and determining, via an audio recognition engine provided by the AI assistant device and based on the environmental sound, that a patient is in distress and is non-responsive.

Other embodiments provide a method that includes capturing, via an Artificial Intelligence (AI) assistant device, audio from an environment, identifying utterances in the audio using the AI assistant device, determining, via an audio recognition engine provided by the AI assistant device, that the utterances indicate that a patient has slurred speech and is non-responsive, and generating an alert via a call system in communication with the AI assistant device.

Other embodiments provide a method that includes capturing, via an Artificial Intelligence (AI) assistant device, audio from an environment, identifying utterances in the audio using the AI assistant device, determining, via an audio recognition engine provided by the AI assistant device, that the utterances captured indicate that a patient is choking, and generating an alert via a call system in communication with the AI assistant device.

The following description and the related drawings set forth in detail certain illustrative features of one or more embodiments.

DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Embodiments herein determine when to place, and then placing, a passive assistive call using personal artificial intelligence (AI) assistants. Assistant devices, by which various personal AI assistants are deployed, offer several benefits over previous assistive call systems, including the ability to use audio recorded in the environment to passively assess the condition of the persons in the environment. The assistant device may be in communication with various other sensors to enhance or supplement the audio assessment of the persons in the environment, and may be used in a variety of scenarios where prior call systems struggled to quickly and accurately identify distress in various monitored persons (e.g., patients) including falls, stroke onset, and choking.

AI assistants provide a bevy of services to their users. These services can include responding to voice-activated requests (e.g., responding via audio to a request for the day's forecast with a local weather prediction), integrating with a human user's calendar, controlling appliances or lights, placing phone calls, or the like. These AI assistants often reside partially on a local device, as a local client, and partially in a back-end service located remotely (e.g., in a cloud server) from the local device. The local client handles data collection, some preprocessing, and data output, while the back-end service may handle speech recognition, natural language processing, and data fetching (e.g., looking up the requested weather forecast).

However, assistant devices, although beneficial in the environment, are active devices that often require the users to speak an utterance with a cue phrase to activate the device or require active input from the users to perform various tasks. Accordingly, although the assistant device can be unobtrusive, and users may seek to incorporate the assistant devices in various environments, the assistant devices often purposely exclude audio not related to human speech from collection and analysis. In contrast, the present disclosure improves upon the base functionalities of the assistant devices by monitoring the usually discarded or filtered-out environmental sounds to identify when a person is in distress to automatically issue an assistive call in addition to or alternatively to monitoring user speech for active commands to place assistive calls.

Accordingly, the present disclosure provides for improved functionality in assistant devices and devices linked to the assistant devices, improved processing speed, improved data security, and improved outcomes in healthcare (including prophylactic care and improved accuracy in diagnoses and treatments).

Example Use Environment

Figure 1:
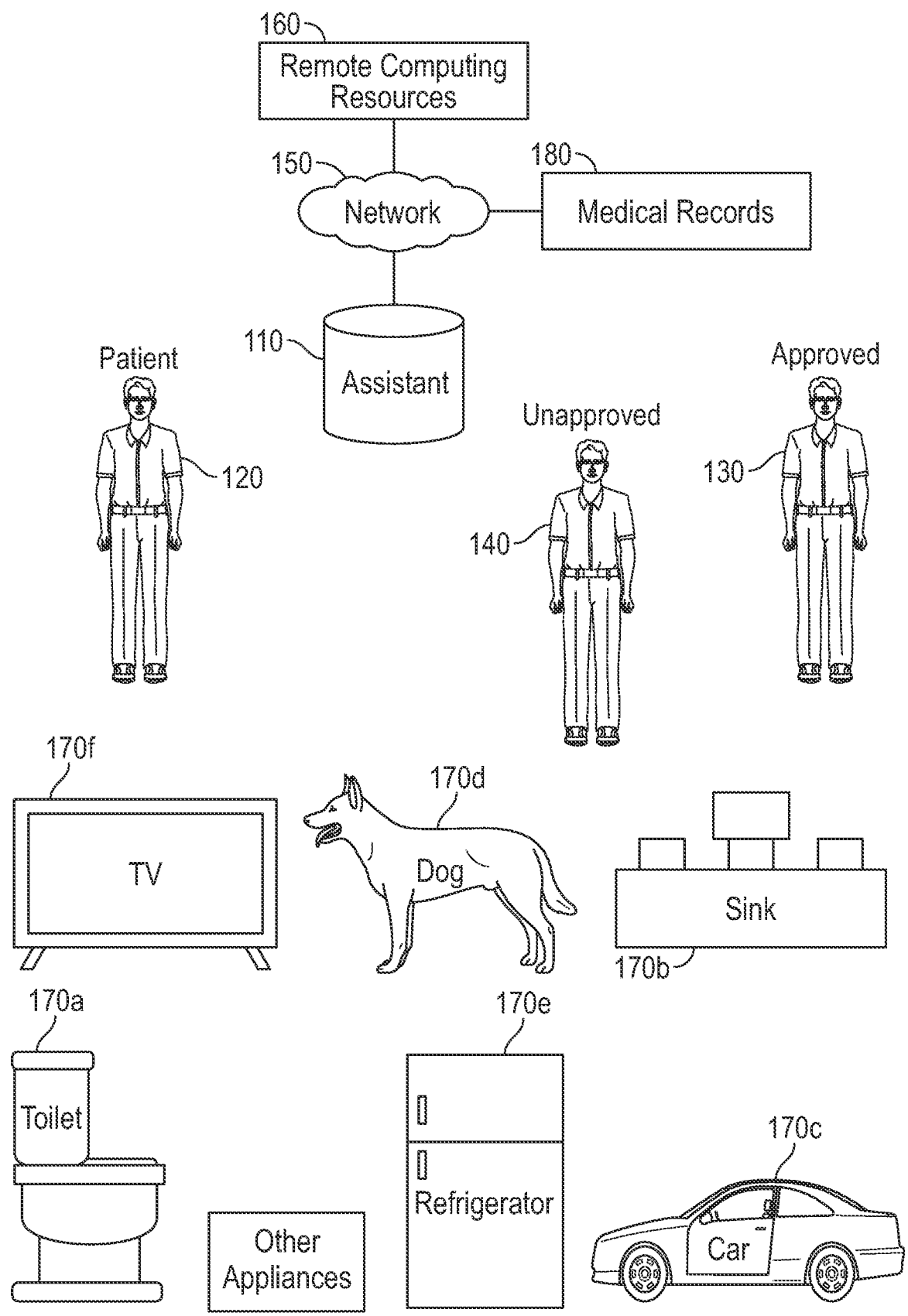
FIG. 1 illustrates an environment in which an assistant device, hosting a local client for an AI assistant, may be deployed to interact with various persons, according to embodiments of the present disclosure.

FIG. 1 illustrates an environment 100 in which an assistant device 110, hosting a local client for an AI assistant, may be deployed to interact with various persons, according to embodiments of the present disclosure. As discussed herein, the environment 100 is a residential environment, such as a personal home, a group home, a care facility, a community center, a car, a store, or other community area. Various persons may come and go in the environment 100 with different levels of access to health information. The environment 100 generally refers to the surrounding areas in which audio outputs of the assistant device 110 are comprehensible to a person of average hearing (unaided by listening devices), and the boundary of the environment 100 may be defined by a Signal to Noise Ratio (SNR) in decibels (dB) for output audio that may change as the volume of the assistant device 110 changes or as background noise changes.

In a healthcare context, the persons that an assistant device 110 may interact with include patients 120 whose health and well-being are monitored, authorized persons 130 who are currently authorized by the patients 120 to receive health information related to the patient 120 via the assistant device 110, and unauthorized persons 140 who are not currently authorized by the patients 120 receive health information related to the patient 120. In various embodiments, the authorized persons 130 and the unauthorized persons 140 may be permitted to interact with the assistant device 110 (or denied access to the assistant device 110) for non-healthcare related information independently of the permissions granted/denied for receiving health information related to the patient 120. Various other objects 170a-f (generally or collectively, objects 170) may also be present in the environment 100 or otherwise be observable by the assistant device 110 including, but not limited to: toilets 170a, sinks 170b, cars 170c, pets 170d, appliances 170e, audio sources 170f (e.g., televisions or radios), etc.

As used herein, a patient 120 may be one of several persons in the environment 100 to whom medical data and personally identifiable information (PII) pertain. Generally, a patient 120 is an authorized user for accessing their own data, and may grant rights for others to also access those data or to grant additional persons the ability to access these data on behalf of the patient 120 (e.g., via medial power of attorney). For example, a patient 120 may grant a personal health assistant, a nurse, a doctor, a trusted relative, or other person the ability to access medical data and PII. A patient 120 may also revoke access to the medical data and PII and may grant or revoke access to some or all of the data. Accordingly, a patient 120 is a person that the medical data and PII relate to, authorized persons 130 are those with currently held rights to access some or all of the medical data and PII, and unauthorized persons 140 include those who have not yet been identified as well as those currently lacking rights to access the medical data and PII. The identification and classification of the various persons is discussed in greater detail in relation to FIG. 2.

The assistant device 110 offers a user interface for requesting and receiving controlled access to health information. In some embodiments, the assistant device 110 is an audio-controlled computing device with which the users may interact with verbally, but various other devices may also be used as a user interface to request or provide health information to authorized parties in the environment. For example, a television may be used to output health information via a video overlay, a mobile telephone may be used to receive requests via touch-input and output health information via video or audio, etc. Generally, the assistant device 110 can be any device capable of hosting a local instance of an AI assistant and that remains in an "on" or "standby" mode to receive requests and provide outputs related to health information while remaining available for other tasks. For example, the assistant device 110 may also handle home automation tasks (e.g., controlling a thermostat, lights, appliances) on behalf of a user or interface with the television to provide health information while the patient 120 is watching a program. Example hardware for an assistant device 110 is discussed in greater detail in regard to FIG. 9.

In various embodiments, the assistant device 110 captures audio in the environment 100 and, to determine how to respond to the captured audio, may locally process the audio, may be in communication with remote computing resources 160 via a network 150 to process the audio remotely, or may perform some audio processing locally and some audio processing remotely. The assistant device 110 may connect to the network 150 via wired technologies (e.g., wires, fiber optic cable, etc.), wireless technologies (e.g., WIFI, cellular, satellite, Bluetooth, etc.), or combinations thereof. The network 150 may be any type of communication network, including data and/or voice networks, local area networks, and the Internet.

To determine how or whether to respond to audio captured in the environment, the assistant device 110 may need to filter out unwanted noises from desired audio, identify the source of the audio, and determine the content of the audio. For example, if the assistant device 110 detects audio of a request for the next scheduled doctor's appointment for the patient 120, the assistant device 110 may need to determine whether the request was received from an audio source 170f as unwanted noise (e.g., a character speaking in a movie or television program), the patient 120, an authorized person 130 (e.g., an in-home care assistant looking up care details for the patient 120), or an unauthorized person 140 (e.g., a curious visitor without authorization to receive that information from the assistant device 110). Other filters may be used to identify and discard sounds made by various other objects 170 in the environment 100.

In order to identify the content of the desired audio (e.g., a command to the assistant device 110), an audio recognition (AR) engine performs audio analysis/filtering and speech recognition on the captured audio signals and calculates a similarity between any audio identified therein and known audio samples (e.g., utterances for certain desired interactions). The AR engine then compares this similarity to a threshold and, if the similarity is greater than the threshold, the AR engine determines that a known audio cue has been received from the environment. The AR engine may use various types of speech and audio recognition techniques, such as, large-vocabulary speech recognition techniques, keyword spotting techniques, machine-learning techniques (e.g., support vector machines (SVMs)), neural network techniques, or the like. In response to identifying an audio cue, the assistant device 110 may then use the audio cue to determine how to next respond. Some or all of the audio processing may be done locally on the assistant device 110, but the assistant device 110 may also offload more computationally difficult tasks to the remote computing resources 160 for additional processing.

In various embodiments, the assistant device 110 may also access health records 180 via the network 150 or may store some health records 180 locally for later access. The health records 180 may include one or more of: medical histories for patients, upcoming or previous appointments, medications, personal identification information (PII), demographic data, emergency contacts, treating professionals (e.g., physicians, nurses, dentists), medical powers of attorney, and the like. The health records 180 may be held by one or more different facilities (e.g., a first doctor's office, a second doctor's office, a hospital, a pharmacy) that the assistant device 110 authenticates with to receive the data. In some embodiments, the assistant device 110 may locally cache some of these health records 180 for offline access or faster future retrieval. Additionally or alternatively, a patient 120 or authorized person 130 can locally supply the medical data, such as by requesting the assistant device 110 to "remind me to take my medicine every morning", importing a calendar entry for a doctor's appointment from a linked account or computer, or the like.

Additionally, the assistant device 110 may store identifying information to distinguish the patient 120, authorized persons 130, and unauthorized persons 140 when deciding whether to share the health records 180 or data based on the health records 180.

Figure 2:
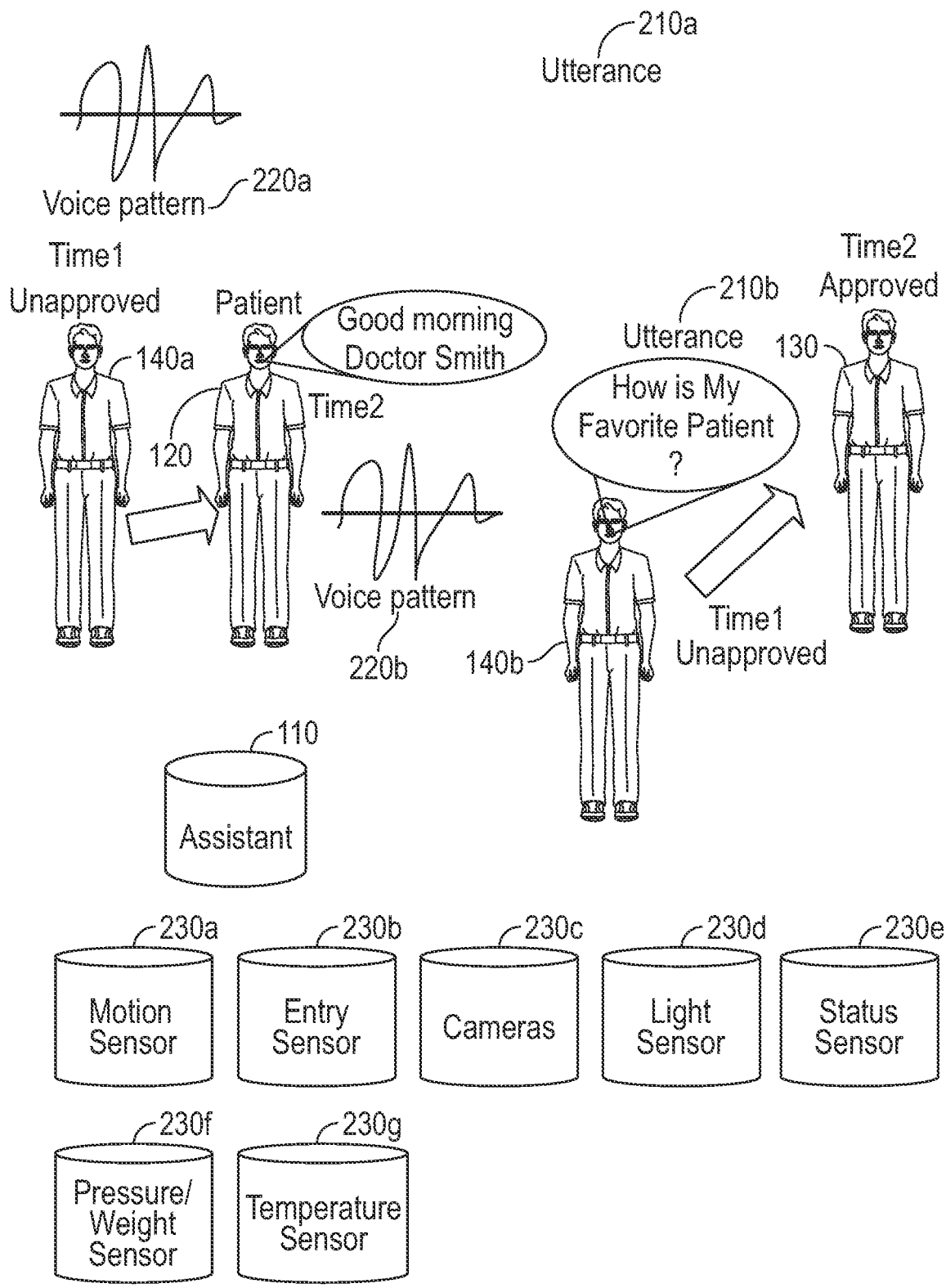
FIG. 2 illustrates an environment in which an assistant device may be deployed when identifying various parties and determining how to respond, according to embodiments of the present disclosure.

FIG. 2 illustrates an environment 200 in which an assistant device 110 may be deployed when identifying various parties and determining how to respond, according to embodiments of the present disclosure. The assistant device 110 can identify or infer the presence of a person in the environment 200 based on received audio containing speech, the sound of a door into the environment opening, or additional presence data received from sensors 230*a-g* (generally or collectively, sensors 230) in the environment, such as a motion sensor 230*a*, an entry sensor 230*b* at a doorway, cameras 230*c*, light sensors 240*d*, or the like. Other sensors 230 that may provide additional input to the assistant device 110 can include on/off status sensors 230*e* (e.g., for specific appliances or electrical circuits), pressure or weight sensors 230*f*, temperature sensors 230*g*, etc. The various sensors 230 may include or be part of a computing system 900 as described in greater detail with regards to FIG. 9.

Generally, until a person has been identified, the assistant device 110 classifies that person as an unauthorized person 140 and may ignore commands or audio from that person. For example, at Time1, the assistant device 110 may know that two persons are present in the environment 200, but may not know the identities of those persons, and therefore treats the first person as a first unauthorized person 140*a* and the second person as a second unauthorized person 140*b*.

In various embodiments, persons can identify themselves directly to the assistant device 110 or may identify other parties to the assistant device 110. For example, when a first utterance 210*a* (generally or collectively, utterance 210) is received from the first unauthorized person 140*a*, the assistant device 110 may extract a first voice pattern 220*a* (generally or collectively, voice pattern 220) from the words (including pitch, cadence, tone, and the like) to compare against other known voice patterns 220 to identify an associated known person. In the illustrated example, the first voice pattern 220*a* matches that of a patient 120, and the assistant device 110 therefore reclassifies the first unauthorized person 140*a* to be the patient 120.

The assistant device 110 may store various identity profiles for persons to identify those persons as a patient 120, authorized persons 130 for that patient, or as unauthorized persons 140 for that patient, with various levels of rights to access or provide health information for the patient 120 and various interests in collecting or maintaining data related to that person.

Once a person has been identified as a patient 120 (or other authorized party trusted to identify other persons with whom access should be granted), the assistant device 110 may rely on utterances 210 from that trusted person to identify other persons. For example, the first utterance 210*a* can be used to identify the first unauthorized person 140*a* as the patient 120 based on the associated first voice pattern 220*a*, and the contents of the first utterance 210*a* can be examined for information identifying the other party. In the illustrated example, the assistant device 110 (either locally or via remote computing resources 160) may extract the identity "Dr. Smith" from the first utterance 210*a* to identify that the second unauthorized person 140*b* is Dr. Smith, who is an authorized person 130 for the patient 120, and the assistant device 110 therefore reclassifies the second unauthorized person 140*b* to be an authorized person 130 for the patient 120.

Additionally or alternatively, the assistant device 110 may identify Dr. Smith as an authorized person 130 based on a second voice pattern 220*b* extracted from the second utterance 210*b* spoken by Dr. Smith. The voice patterns 220 may be continuously used by the assistance device 110 to re-identify Dr. Smith or the patient 120 (e.g., at a later time) within the environment 200 or to distinguish utterances 210 as coming from a specific person within the environment 200.

When multiple persons are present in the environment 200, and potentially moving about the environment, the assistant device 110 may continually reassess which person is which. If a confidence score for a given person falls below a threshold, the assistant device 110 may reclassify one or more persons as unauthorized persons 140 until identities can be reestablished. In various embodiments, the assistant device 110 may use directional microphones to establish where a given person is located in the environment 200 and may rely on the various sensors 230 to identify how many persons are located in the environment 200 and where those persons are located.

Example Fall Scenarios

FIGS. 3A-3D illustrate example scenarios for how an AI assistant device 110 may be used to passively call for assistance in response to identifying that a patient 120 has fallen and is non-responsive, according to embodiments of the present disclosure. As will be appreciated, the assistant device 110 may also actively be used to call for assistance in response to receiving a command from a person in the environment 300 (e.g., "call an ambulance for me!"), and the commands issued to the assistant device 110 may be received from various patients 120 for themselves or from authorized persons 130 on behalf of the patients 120. As used herein, a person who is "non-responsive" can be unresponsive (e.g., not providing responses), but may also include scenarios where the person is attempting to provide a response that is otherwise unintelligible or irrelevant to queries posed to that person (e.g., a person crying too hard to be understood, a person with slurred or disjointed speech, a person shouting expletives instead of answers to a question, etc.).

In each of FIGS. 3A-3D, an assistant device 110 is present in the environment 300 and captures audio. A machine learning model provided by the assistant device 110 can filter or divide the captured audio into two classes: speech sounds or utterances 210 and environmental sounds 310. The machine learning model may focus on certain frequency ranges based on demographic characteristics of the patient 120 that affect voice frequency (e.g., age, gender, smoking habits, pulmonary or vocal medical conditions) to identify a fundamental frequency (e.g., between 85 and 255 Hertz (Hz) for adults) and harmonics (e.g., between 30 and 3500 Hz for adults) therein to identify speech sounds. Sounds not identified as related to speech, however, are retained for further analysis as environmental sounds 310. Frequency filtering is given as a non-limiting example for dividing captured audio into speech sounds and environmental sounds 310, but additional filtering is contemplated to identify environmental sounds 310 within the frequency range of human speech and elements of human speech outside of the main ranges used for speech.

The assistant device 110 provides an audio recognition engine, which may be another machine learning model or an additional layer of the filtering machine learning model, that is trained to match various environmental sounds 310 against known sound classes for events occurring in the environment 300. For example, when trained to identify environmental sounds 310 as one of a person falling down, a person performing an eating behavior, a door opening, or none of the identified events (e.g., not a person falling down, not a person performing an eating behavior, and not a door opening), the audio recognition engine receives the audio, pre-processes the audio, and determines which class the pre-processed audio best matches to, thereby identifying the event (or non-event) that the environmental sound 310 indicates.

In addition to processing and classifying the environmental sounds 310 to identify events occurring in the environment 300, in some embodiments, the audio recognition engine may include speech recognition for various key phrases. For example, various preloaded phrases may be preloaded for local identification by the assistant device 110, such as, a name of the AI assistant to activate the assistant device 110 (e.g., "Hey, HAL") or phrases to deactivate the assistant device 110 (e.g., "never mind", "I'm fine", "cancel request", etc.). The assistant device 110 may offload further processing of speech sounds to a speech recognition system offered by remote computing resources 160 to identify the contents and intents of the various utterances 210 captured in the environment 300.

The audio recognition engine can use a variety of different machine learning algorithms or models to perform the functions described herein. In one embodiment, the audio recognition engine uses a deep-learning-based trigger model. The audio recognition engine can use any suitable natural language processing (NLP) machine learning algorithm. Further, the machine learning algorithm can be trained to recognize deviations in the patient's voice pattern such as when the patient's speech becomes slurred. The AI assistant device 110 can use the patient's own voice as training data to perform supervised learning. For example, the AI assistant device 110 may, when first being started, ask the patient to perform a baseline test to generate the training data so the AI assistant device 110 can later detect deviations in the patient's voice or speech pattern.

When the assistant device 110 identifies that a patient 120 has performed an action via audio cues from the environment 300, the assistant device 110 may supplement the audio determination with various non-audio sensors (e.g., motion sensors, camera sensors, biometric sensors), or a supplemental audio response from the patient 120. In various embodiments, the assistant device 110 may wait a predefined amount of time to hear an utterance 210 from the patient 120 indicating that the patient 120 is alright and may prompt the patient 120 to provide such a reassurance. However, if the patient 120 is non-responsive within this time window, the assistant device 110 may generate an alert via a call system 340 to indicate that the patient 120 is in distress to various authorized persons 130 who are associated with personal devices 330 that receive the alert.

Although the assistant device 110 may receive utterances 210 with identifiable speech after an event that induces distress in the patient 120 (such as a fall) is detected, the patient 120 may still be classified as non-responsive. For example, when a patient 120 falls, they may be in great pain and shouting various words (e.g., expletives, pain signalers such as "ouch" or "ow"), but cannot respond to outside stimuli or currently form a structured request for help. Accordingly, the assistant device 110 may determine both that a distress-inducing event has occurred and that (as a result) the patient 120 is non-responsive before generating an alert.

In various embodiments, the assistant device 110 transmits the alert to a call system 340 to propagate according to various transmission protocols to one or more personal devices 330 associated with authorized persons 130 to assist the patient 120. Example hardware as may be used in the call system 340 and the personal devices 330 can include a computing system 900 as is discussed in greater detail in FIG. 9. In some embodiments, the call system 340 is connected to a telephone network and pushes the alerts as one or more individual messages sent to a corresponding one or more personal devices 330 that are cellphones or pagers via text messages (e.g., via Short Message Service (SMS) or Multimedia Message Service (MMS)) or phone calls using a synthesized voice to alert the authorized persons 130 that the patient 120 is in distress. Additionally or alternatively, when the call system 340 is part of an alert system in a group home or medical facility, the call system 340 can transmit the alert via a broadcast message to be received by personal devices 330 associated with caretakers (as example authorized persons 130) in the group home or medical facility.

Figure 3A:
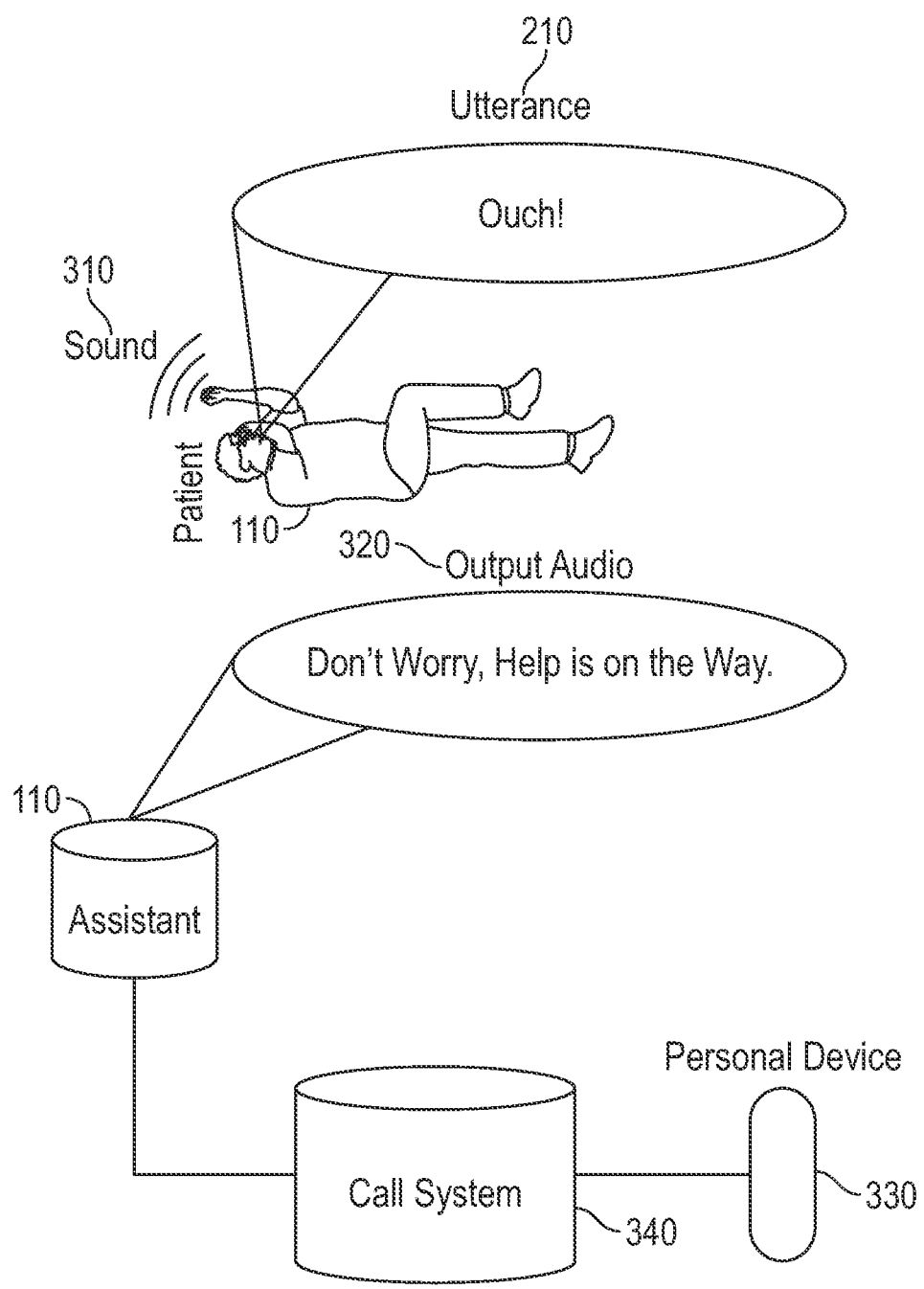
FIGS. 3A-3D illustrate example scenarios for how an AI assistant device may be used to passively call for assistance in response identifying that a patient has fallen, according to embodiments of the present disclosure.

FIG. 3A illustrates a first scenario where an assistant device 110 captures audio from the environment 300 indicative that a patient 120 has fallen as indicated by both an utterance 210 and an environmental sound 310. As illustrated, an environmental sound 310 of the patient 120 hitting the floor precedes the utterance of "ouch!" from the patient 120. In response to the sequence of audio from the environment 300 indicating that the environmental sound 310 is a fall sound, and that the patient 120 is hurt, the assistant device 110 generates an audio output 320 of "Don't worry, help is on the way". When the patient 120 does not respond, either on their own or in response to the audio output 320, within a response window, the assistant device 110 may then generate an alert for the call system 340 to transmit to the relevant personal devices 330.

Figure 3B:
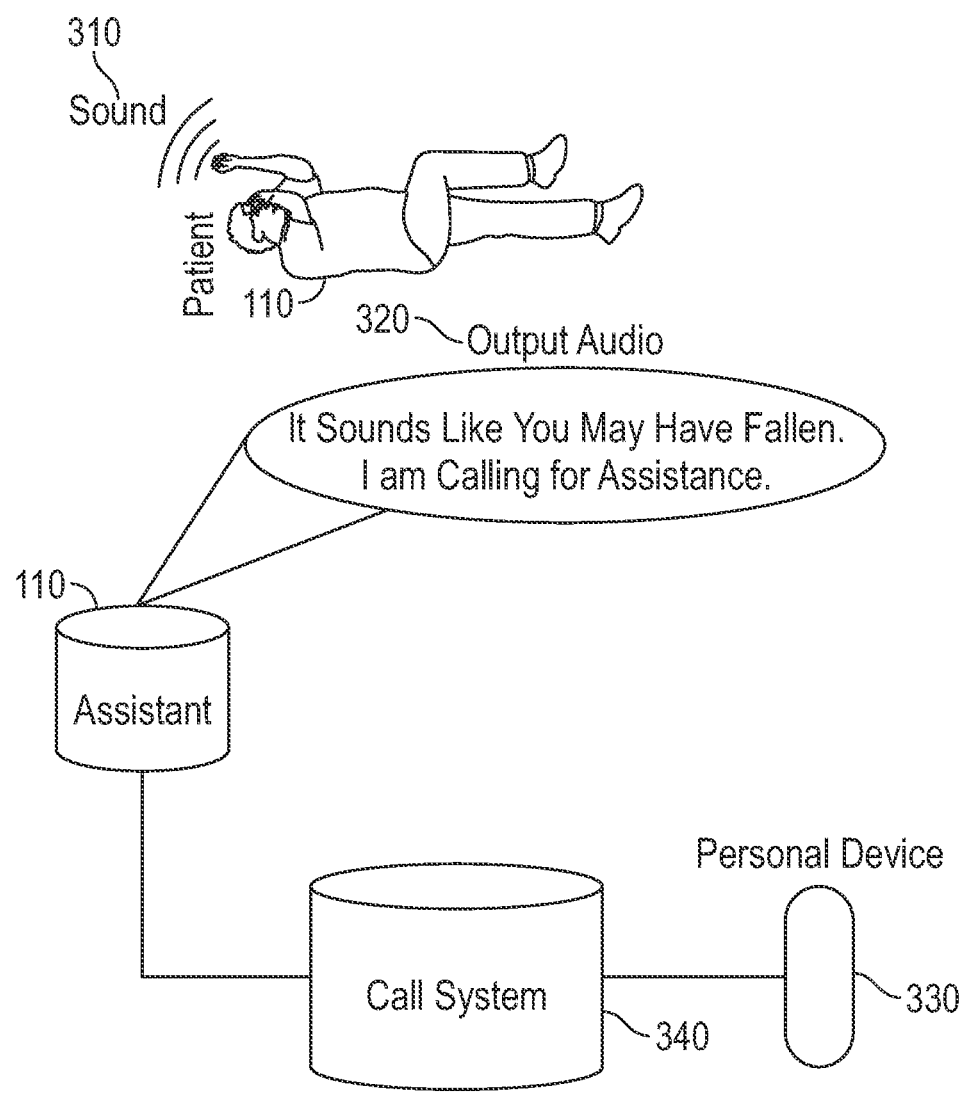

FIG. 3B illustrates a second scenario where an assistant device 110 captures audio from the environment 300 indicative that a patient 120 has fallen as indicated by both the lack of an utterance 210 and an environmental sound 310. As illustrated, an environmental sound 310 of the patient 120 hitting the floor is captured, but no utterance is received from the patient 120 (who may be unconscious). In response to the environmental sound 310 matching a fall sound, the assistant device 110 generates an audio output 320 of "It sounds like you may have fallen. I am calling for assistance" to prompt the patient 120 to respond. When the patient 120 does not respond, either on their own or in response to the audio output 320, within a response window, the assistant device 110 may then generate an alert for the call system 340 to transmit to the relevant personal devices 330.

Figure 3C:
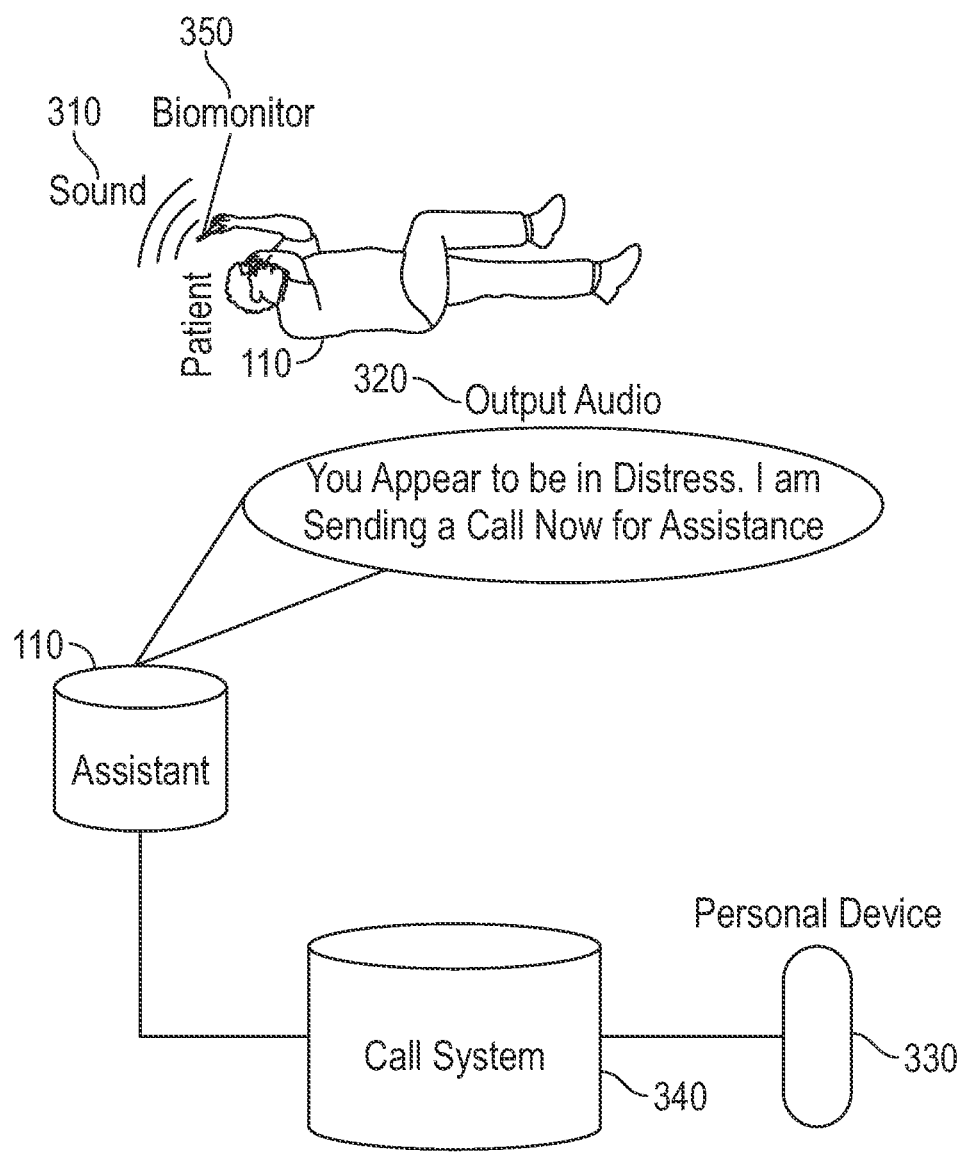

FIG. 3C illustrates a third scenario where an assistant device 110 captures audio from the environment 300 indicative that a patient 120 has fallen as indicated by an environmental sound 310 and a supplemental reading from a biometric monitor 350. As illustrated, an environmental sound 310 of the patient 120 hitting the floor is captured, but no utterance is received from the patient 120 (who may be unconscious). In response to the environmental sound 310 matching a fall sound, the assistant device 110 may request supplemental data from various sensors (e.g., cameras, motion sensors, etc.,) in the environment 300 or associated with the patient 120 to determine whether the patient 120 is in distress. In various embodiments, the biometric monitor 350 is a computing system 900, such as that discussed in relation to FIG. 9, with additional sensors to measure the heart rate, breathing rate, or other vital sign of the patient 120. Supplemental data indicating that the patient 120 is in distress may include: heart rates outside of a healthy range (e.g., tachycardia, bradycardia), breathing rates outside of a normal range (e.g., tachypnea, bradypnoea), the patient 120 being immobile, the presence of blood or other bodily fluids near or on the patient 120, and other conditions that the assistant device 110 is trained to recognize.

In response to the environmental sound 310 matching a fall sound and the supplemental data indicating that the patient 120 is in distress, the illustrated assistant device 110 generates an audio output 320 of "You appear to be in distress. I am sending a call now for assistance" to prompt the patient 120 to respond. When the patient 120 does not respond, either on their own or in response to the audio output 320, within a response window, the assistant device 110 may then generate an alert for the call system 340 to transmit to the relevant personal devices 330.

Figure 3D:
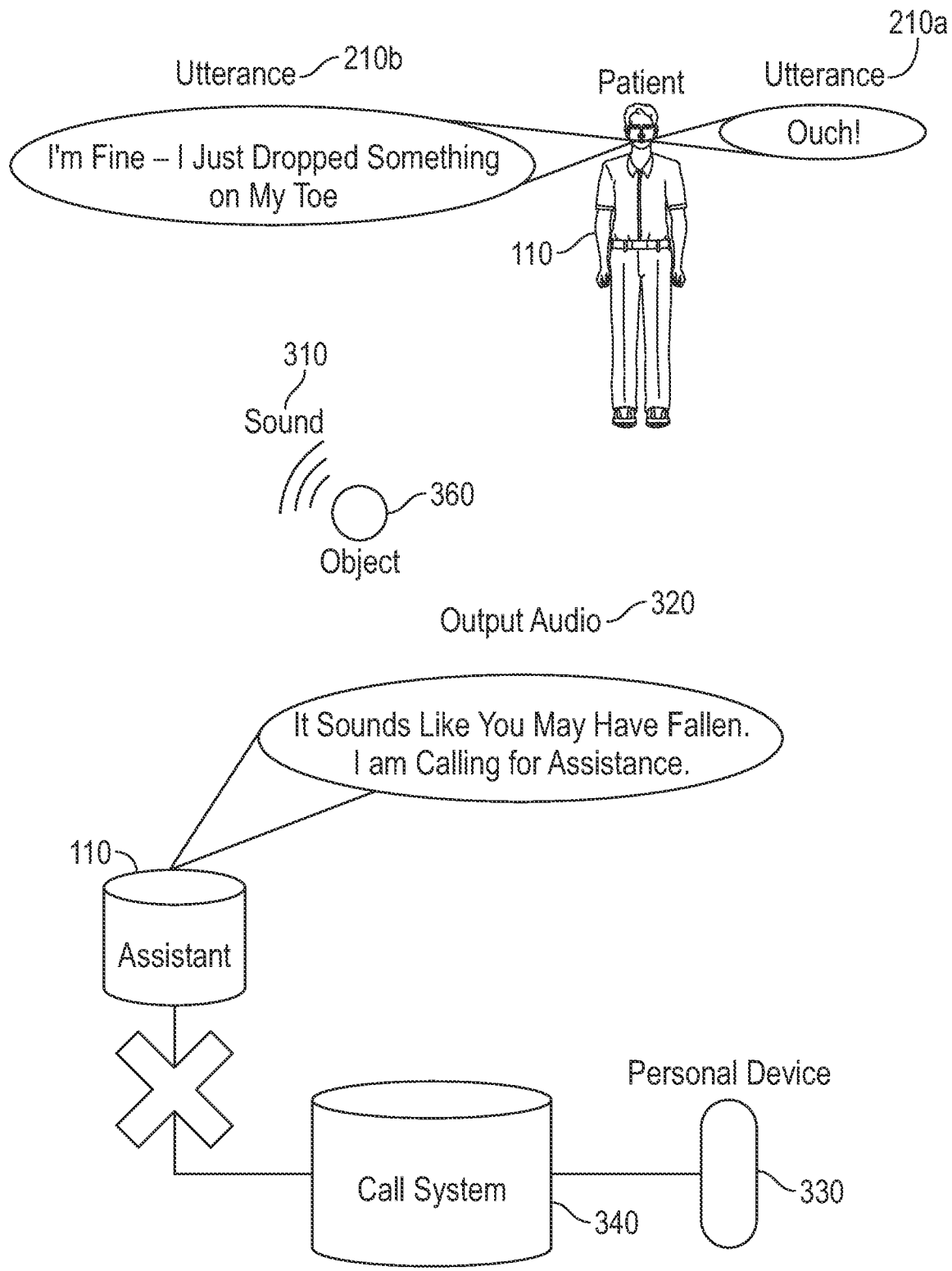

FIG. 3D illustrates a fourth scenario where an assistant device 110 captures audio from the environment indicative that a patient 120 has fallen as indicated by both a first utterance 210a and an environmental sound 310 but is superseded by the patient 120 in a second utterance 210b. As illustrated, an environmental sound 310 of an object 360 hitting the floor precedes a first utterance 210a of "ouch!" from the patient 120, which the assistant device 110 interprets to indicate that the patient 120 has fallen and is in distress (similarly to the first scenario of FIG. 3A).

In response to the sequence of audio from the environment 300 indicating that the environmental sound 310 is a fall sound, and that the patient 120 is hurt, the assistant device 110 generates an audio output 320 of "It sounds like you may have fallen. I am calling for assistance". However, the patient 120 responds within a response window with a second utterance 210b of "I'm fine—I just dropped something on my toe". Accordingly, either through local identification of a cancellation cue in the second utterance 210b or remotely determined contents or intent of the second utterance 210b via a remote speech processing system, the assistant device 110 is signaled that the patient 120 is responsive, and that an automated alert should not be generated.

Figure 4:
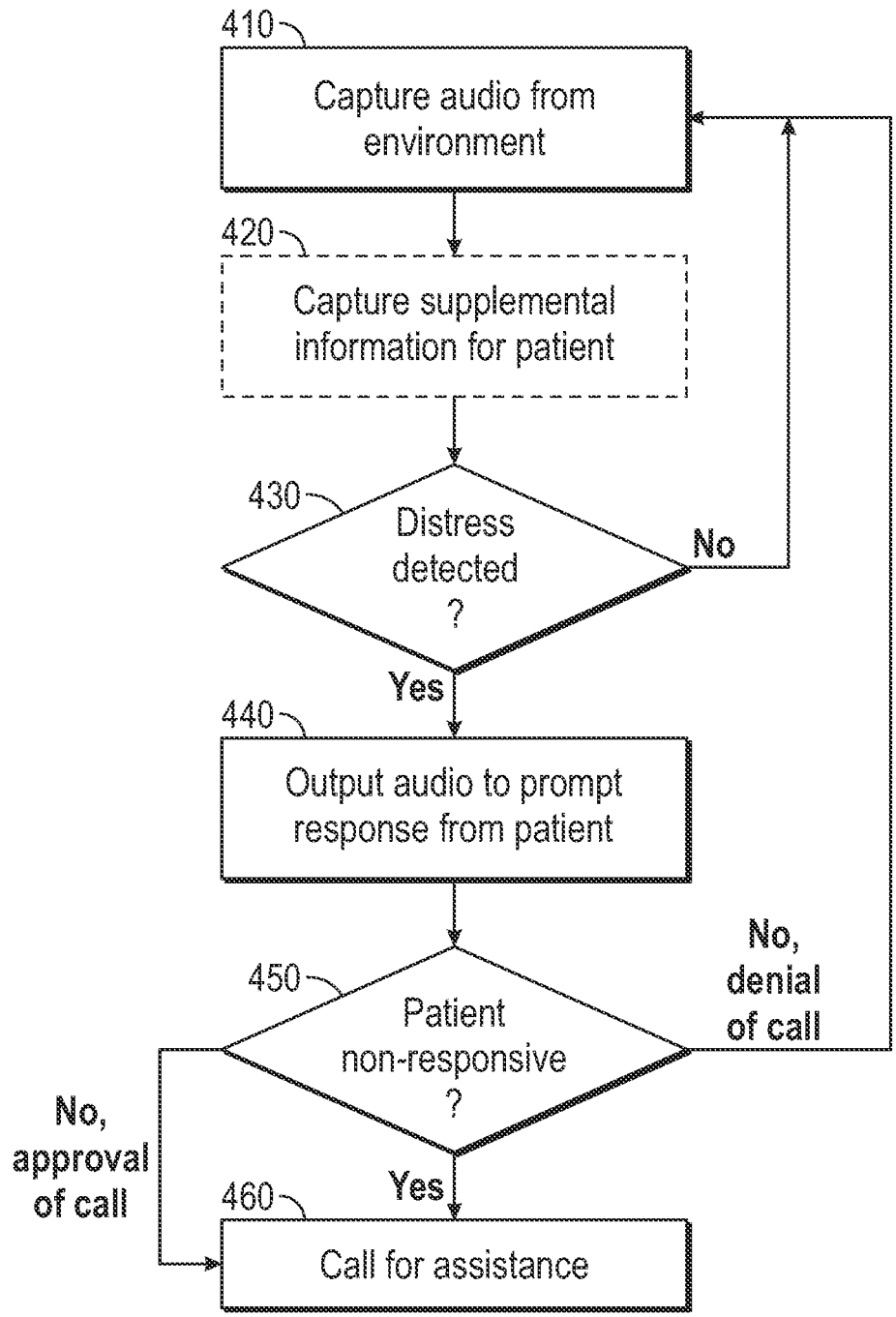
FIG. 4 is a flowchart of a method for passively identifying that a patient has fallen and responding to the determination, according to embodiments of the present disclosure.

FIG. 4 is a flowchart of a method 400 where an assistant device passively identifies and responds to a patient falling, according to embodiments of the present disclosure. Method 400 begins at block 410, where the assistant device captures audio from an environment. In various embodiments, the assistant device may constantly capture audio from the environment as part of a "listening mode" used to wait for an activation cue to transition to an "active mode" to begin reacting to utterances with commands from a user to the assistant device. The audio received while in the "listening mode" may ordinarily be discarded by various assistant devices, but when analyzed according to the present disclosure, the audio is used to improve the functionality of the assistant device to passively identify when a patient is in distress and call for assistance on behalf of the patient. In various embodiments, a user can enable (or disable) a "passive assistance mode" in the assistant device to perform (or not perform) method 400. In various embodiments, a machine learning model provided by the assistant device filters the captured audio into two classes of sounds: environmental sounds and utterances (also referred to as speech sounds).

At block 420, the assistant device optionally captures supplemental information for the patient. In various embodiments, the supplemental information can include data collected from non-audio sensors in the environment (e.g., images of the patient and surroundings) that are analyzed for various evidence of the patient having fallen (e.g., position and location of the patient, the presence of bodily fluids on or near the patient). Additionally or alternatively, the assistant device interfaces with various biometric monitors associated with the patient to receive data such as heart rate, breathing rate, etc., to supplement a determination that the patient is in distress of non-responsive.

In various embodiments, the assistant device may refrain from capturing the supplemental information until an audio cue is received that indicates that the patient may be in distress, but the assistant device is unsure based on the audio cue alone. For example, the assistant device may initially determine from the audio data whether the patient is in distress and non-responsive (per block 430) and when the audio data indicate a confidence that the patient is in distress and non-responsive between a first threshold (e.g., a potentiality threshold) and a second threshold (e.g., a certainty threshold), the assistant device may prompt the other sensors for additional information to raise or lower the confidence to alert or not alert, respectively. Accordingly, the assistant device may improve the computing efficiency of the sensors and network efficiency for communicating with the sensors by not capturing supplemental data (and thereby not requiring computing resources or network resources) unless the audio cues are ambiguous for whether the patient is in distress.

At block 430, the assistant device, via an audio recognition engine, determines whether the patient is in distress. In various embodiments, to provide unobtrusive analysis of the patient and reduce the need for (and computational resources used by) additional sensors, such as imaging systems that infringe on a patient's privacy, in one embodiment the assistant device initially attempts to identify whether the patient is in distress solely via audio cues from the environment. For example, an audio recognition engine provided locally by the assistant device analyzes various environmental sounds with known triggers for distress in patients, such as the sound of a person falling and hitting the ground. The audio recognition device may analyze several sounds in a series or collection to indicate that the patient is in distress to avoid false positives from a single environmental cue.

For example, a patient with a heavy footfall may generate several environmental sounds similar to a "fall sound", but because a person generally generates footfalls when walking at a faster rate than a person can by repeatedly getting up and falling, a single noisy fall sound may be used to determine that the patient has fallen, while several less noisy fall sounds may be used to determine that the patient is walking. However, several lighter fall sounds followed by one louder fall sound (and no further fall sounds) may be used to determine that the patient was walking, and then fell.

In addition to environmental sounds, the audio recognition engine may analyze utterances from the patient for known reactions to distress to the patient. For example, the audio recognition engine may perform analysis for human generated sounds that are pain signalers, such as "ouch", profanity, crying, or the like. Similarly, the audio recognition engine may denote when the patient is silent, such as when the patient is unconscious.

When the assistant device determines that the patient is not in distress, method 400 returns to block 410 to continue capturing audio from the environment. When the assistant device determines that the patient is in distress (or is believed to be in distress), method 400 proceeds to block 440.

At block 440, the assistant device outputs an audio cue to prompt a response from the patient. In various embodiments, the audio cue uses a synthesized voice that the assistant device outputs via one or more speakers to alert the patient that a call for assistance will be made unless cancelled by the patient.

At block 450, the assistant device determines whether the patient has been non-responsive since the output audio was generated (per block 440) for at least a response threshold amount of time. The patient may be non-responsive even if alert and making utterances, such as when crying in pain, yelling obscenities, or shouting pain signalers. Accordingly, the assistant device may locally analyze any human speech received from the environment during the response window to determine whether any key phrases are received to indicate that the patient is responding to the assistant device and the output audio.

When the patient is non-responsive during the response window, method 400 proceeds to block 460. Similarly, when the patient is responsive, but actively approves of the assistant device calling for assistance, method 400 proceeds to block 460, potentially before the response window expires. For example, when the assistant devices says "It appears you have fallen, I will call for help", and the patient responds "Yes", "Please hurry" or another phrase known to the audio recognition engine to indicate approval, method 400 proceeds to block 460. However, when the patient is responsive, and actively denies the assistant device from following through on generating an alert, method 400 returns to block 410 to continue capturing audio from the environment.

At block 460, after determining that a patient is in distress and is non-responsive or that the patient approves of generating an alert, the assistant device calls for assistance for the patient. In various embodiments, the call for assistance is generated by a call system in communication with the assistant device that places a phone call or a text message to one or more specific personal devices for persons authorized to help the patient. Additionally or alternatively, the call system may transmit one alert as a multicast or broadcast to multiple personal devices (e.g., all devices for on-duty nurses in a healthcare facility) or to a community management device (e.g., a switchboard for a group home, an alert light in a hallway associated with a given room in a hospital, etc.).

Example Stroke Scenarios

Figure 5:
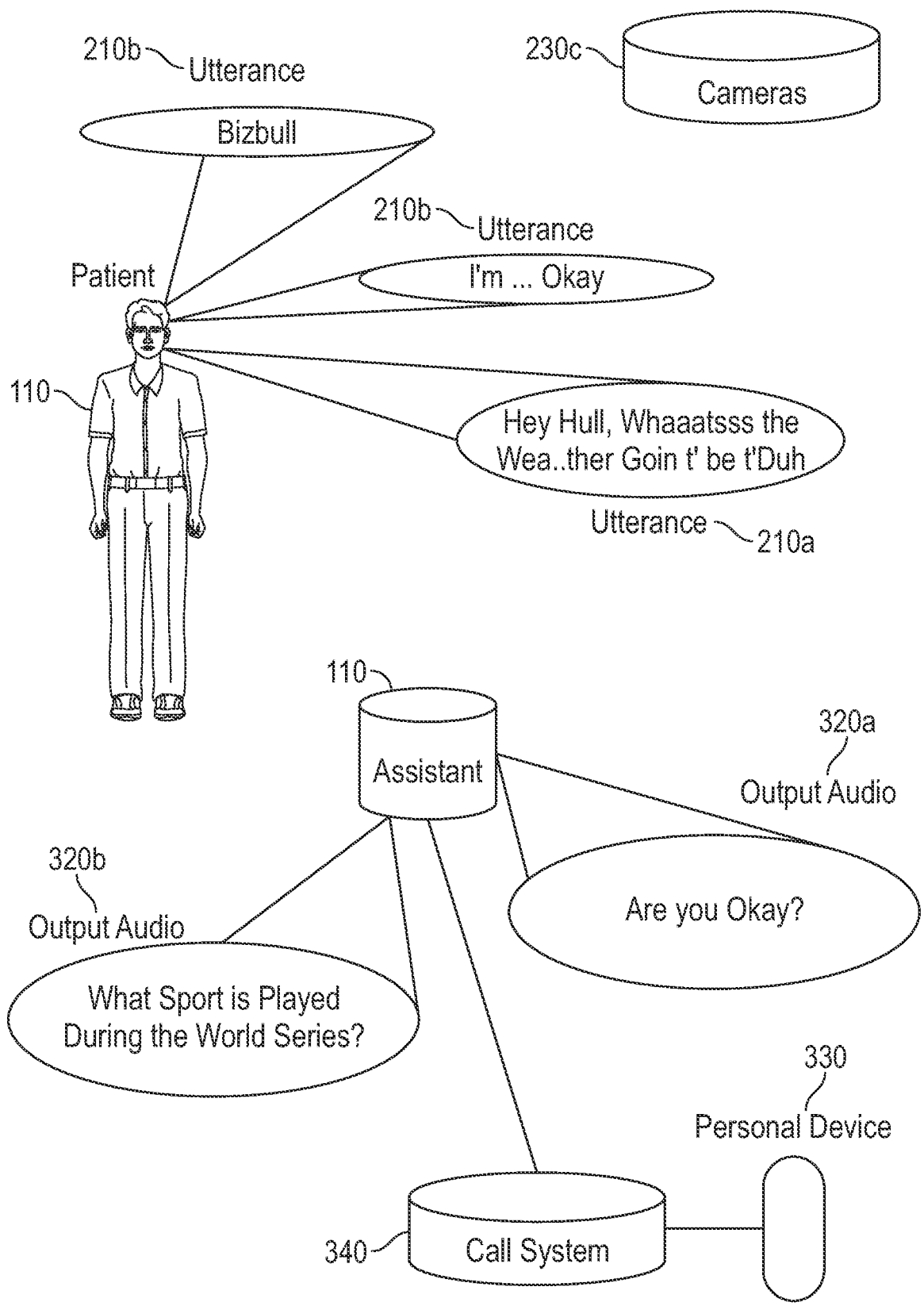
FIG. 5 illustrates an example scenario when an AI assistant device passively calls for assistance in response to identifying that a patient is experiencing a stroke, according to embodiments of the present disclosure.

FIG. 5 illustrates an example scenario where an AI assistant device 110 passively calls for assistance in response to identifying that a patient 120 is experiencing a stroke, according to embodiments of the present disclosure. Additionally or alternatively to monitoring a patient 120 via audio inputs from the patient 120 and the environment 500 for distress due to falls (e.g., as described in relation to FIGS. 3A-3D and 4), the present disclosure improves the functionality of the assistant device 110 to monitor a patient 120 for distress due to stroke. Two of the signs for rapid diagnosis of strokes in patients 120 include slurred or disjointed speech (generally, slurred or slurry speech) and facial paralysis, often on only one side of the face, causing "facial droop", where an expression is present on one side of the face and muscle control has been lost in the lower face and one side of the upper face. Depending on the severity of the stroke in the patient 120, the patient 120 may no longer be able to produce intelligible speech or otherwise actively call for assistance. Accordingly, the assistant device 110 may analyze utterances 210 generated by the patient 120 to determine when to generate an alert for a medical professional to diagnose and aid the patient 120.

As illustrated in FIG. 5, the patient 120 speaks a first utterance 210a intended to convey "Hey HAL, what is the weather going to be today?" to request an assistant device 110 (activated by the cue phrase of "Hey HAL") to respond with a weather forecast. Due to slurring in the patient's speech, the first utterance 210a is disjointed and may be unintelligible or barely intelligible for speech analysis by a speech recognition system. Additionally, because the cue phrase may also be affected, the assistant device 110 may not transition to an active mode to respond to the patient's request for the weather forecast.

Unlike other devices that remain inactive until a cue phrase is clearly received, an assistant device 110 operating according to the present disclosure may continuously monitor the environment 500 for human speech and environmental sounds that would otherwise be discarded or ignored. Using these discarded sounds, an audio recognition engine provided by the assistant device 110 may look for "near misses" for known samples of speech to identify slurring. For example, the first portion of the first utterance 210*a* of "Hey hull" may be compared to the cue phrase of "Hey HAL" to determine that the uttered speech does not satisfy a confirmation threshold for the patient 120 to have spoken "Hey HAL" to activate the assistant device 110, but does satisfy a proximity threshold as being close to intelligibly saying "Hey HAL". When the confidence in matching a received phrase to a known phrase falls between the proximity threshold (as a lower bound) and the confirmation threshold (as an upper bound), and does not satisfy a confirmation threshold for another known phrase (e.g., "Hey hon" to address a loved one as 'hon'), the assistant device 110 may take further action to determine if the patient is in distress.

When the patient 120 is identified as being in distress as possibly suffering a stroke, the assistant device 110 may generate various audio outputs 320 to prompt the patient 120 to provide further utterances 210 to gather additional speech samples to compare against, which may include pre-recorded speech samples from the patient 120 to guard against accents or preexisting speech impediments yielding false positives for detecting a potential stroke.

As illustrated in FIG. 5, the assistant device 110 issues a first audio output 320*a* of "are you okay" to prompt the patient 120 to respond. The patient 120 responds via a second utterance 210*b* of "I'm . . . okay", which the audio recognition engine may compare against a previously supplied utterance of "I'm okay" from the patient 120 to identify that a pause between "I'm" and "okay" in the second utterance 210*b* may be indicative of speech difficulties or slurring.

The assistant device 110 may generate a second audio output 320*b* of "What sport is played during the World Series?" or another pre-arranged question/response pair that the patient 120 should remember the response to. The second audio output 320*b* prompts the patient 120 to reply via a third utterance 210*c*, "Bizbull" to intended to convey the answer of "baseball", albeit with a slurred speech pattern. Similarly, if the patient 120 were to supply an incorrect answer (e.g., basketball) after having established knowledge of the correct answer when setting up the pre-arranged question/response, the mismatch may indicate cognitive impair, even if the speech is not otherwise slurred, which may be another sign of stroke.

When the assistant device 110 detects slurred speech via the utterances 210 almost (but not quite) matching known audio cues or not matching a pre-supplied audio clip of the patient 120 speaking the words, the assistant device 110 may activate various supplemental sensors to further identify whether the patient is in distress. For example, a camera sensor 230 may be activated and the images provided to a facial recognition system (e.g., provided by remote computing resources 160) to identify whether the patient 120 is experiencing partial facial paralysis; another sign of stroke.

Additionally or alternatively, the assistant device 110 may access electronic health records 180 for the patient 120 to adjust the thresholds used to determine whether the slurred speech or facial paralysis is indicative of stroke. For example, when a patient 120 is observed with slurred speech, but the health records 180 indicate that the patient 120 was scheduled for a dental cavity filling earlier in the day, the assistant device 110 may adjust the confidence window upward so that false positives for stroke are not generated due to the facial droop and speech impairment expected from local oral anesthesia. In another example, when the patient 120 is prescribed medications that affect motor control, the assistant device 110 may adjust the confidence window upward so that greater confidence in stroke is required before an alert is generated. In a further example, when the health records 180 indicate that the patient 120 is at an elevated risk for stroke (e.g., due to medications, previous strokes, etc.), the assistant device 110 may adjust the confidence window downward so that lower confidence in stroke is required before an alert is generated.

When the patient 120 has slurred speech and/or exhibits partial facial paralysis sufficient to satisfy the thresholds for stroke, the assistant device 110 determines that the patient 120 is in distress and is non-responsive (despite potentially attempting to be responsive), and therefore generates an alert that the patient 120 is in distress.

In various embodiments, the assistant device 110 transmits the alert to a call system 340 to propagate according to various transmission protocols to one or more personal devices 330 associated with authorized persons 130 to assist the patient 120. Example hardware as may be used in the call system 340 and the personal devices 330 can include a computing system 900 as is discussed in greater detail in FIG. 9. In some embodiments, the call system 340 is connected to a telephone network and pushes the alerts as one or more individual messages sent to a corresponding one or more personal devices 330 that are cellphones or pagers via text messages (e.g., via Short Message Service (SMS) or Multimedia Message Service (MMS)) or phone calls using a synthesized voice to alert the authorized persons 130 that the patient 120 is in distress. Additionally or alternatively, when the call system 340 is part of an alert system in a group home or medical facility, the call system 340 can transmit the alert via a broadcast message to be received by personal devices 330 associated with caretakers (as example authorized persons 130) in the group home or medical facility.

Figure 6:
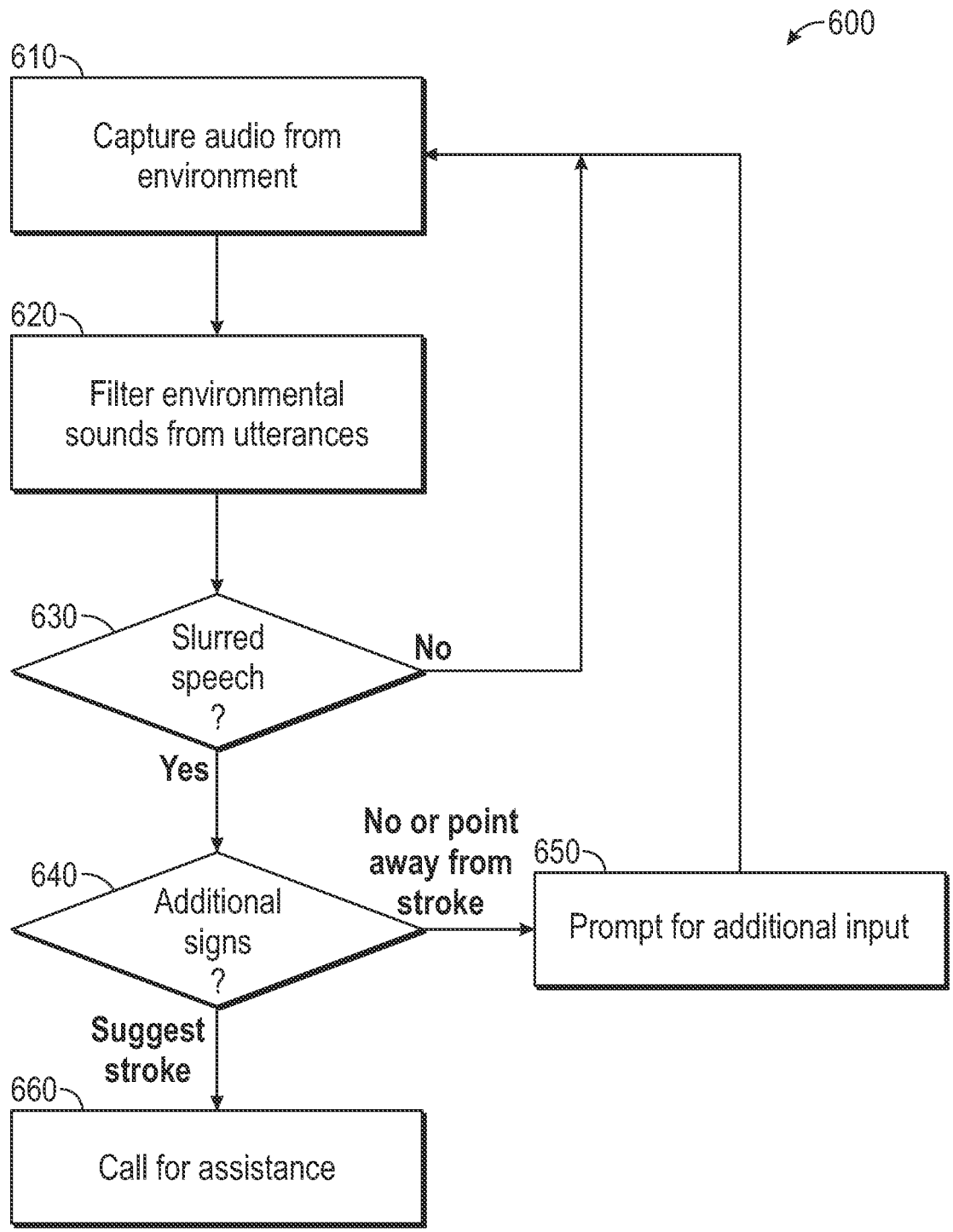
FIG. 6 is a flowchart of a method for passively identifying that a patient is experiencing a stroke and responding to the determination, according to embodiments of the present disclosure

FIG. 6 is a flowchart of a method 600 for passively identifying and responding to a determination that a patient is experiencing a stroke, according to embodiments of the present disclosure. Method 600 begins at block 610, where the assistant device captures audio from the environment. In various embodiments, the assistant device may constantly capture audio from the environment as part of a "listening mode" used to wait for an activation cue to transition to an "active mode" to begin reacting to utterances with commands from a user to the assistant device. The audio received while in the "listening mode" may ordinarily be discarded by various assistant devices, but when analyzed according to the present disclosure, is used to improve the functionality of the assistant device to passively identify when a patient is in distress and call for assistance on behalf of the user. In various embodiments, a user can enable (or disable) a "passive assistance mode" in the assistant device to perform (or not perform) method 600.

At block 620, a machine learning model provided by the assistant device filters the captured audio into two classes of sounds: environmental sounds and utterances (also referred to as speech sounds). The machine learning model may focus on certain frequency ranges based on demographic characteristics of the patient that affect voice frequency (e.g., age, gender, smoking habits, pulmonary or vocal medical conditions) to identify a fundamental frequency (e.g., between 85 and 255 Hz for adults) and harmonics (e.g., between 30 and 3500 Hz for adults) therein to identify speech sounds. Sounds not identified as related to speech, however, are retained for further analysis as environmental sounds. Frequency filtering is given as a non-limiting example for dividing captured audio into speech sounds and environmental sounds, but additional filtering is contemplated to identify environmental sounds within the frequency range of human speech and elements of human speech outside of the main ranges used for speech.

At block 630, an audio recognition engine provided by the assistant device determines whether utterances in the speech sounds received in the audio indicate that a patient has slurred speech. In various embodiments, the audio recognition model identifies whether speech is slurred by comparing received utterances to known phrases to identify "near misses" where a patient is attempting to form an utterance, but in execution, has failed to enunciate the words sufficiently to be understandable as the intended utterance. Accordingly, the audio recognition engine may use two thresholds when analyzing utterances, where a proximity threshold may identify several somewhat similar sounding utterances as "almost" being interpretable as the known phrase (and potentially a slurred version of the known phrase) and a confirmation threshold identifies that the received utterance matches the known phrase.

For example, when the known phrase is an activation cue for the assistant device of "hey HAL", the assistant device may receive various speech sounds that sound somewhat similar to "hey HAL" that satisfy the proximity threshold, such as "hey HAL", "hi HAL" "hey hon", "huh hull", etc. Not all of the speech sounds that satisfy the proximity threshold represent slurred speech. For example, the utterance of "hey HAL" that exactly matches the known phrase of "hey HAL" satisfies the proximity threshold and the confirmation threshold. Similarly, the intended utterance of "hey hon" may match a confirmation threshold for a different known phrase" (e.g., to attract the attention a person referred to as "hon" by the speaker). Accordingly, when an utterance satisfies a confirmation threshold, the assistant device may determine that the speech is not slurred.

Continuing the example, because slurring due to stroke may affect different phonemes in different ways, the audio recognition engine may determine that some speech that satisfies the proximity threshold but does not satisfy any confirmation thresholds as non-indicative to slurred speech. Generally, slurring of speech due to stroke elongates vowel sounds (e.g., changing "i" to "ɨ" or "e" to "ə", etc., per International Phonetic Alphabet (IPA) notation) and softens various consonant sounds (e.g., changing "t" to "d", "j" to "щ", "k" to "g", etc., per IPA notation). Accordingly, the audio recognition engine may identify when the "near miss" satisfies the proximity threshold is a muddled or softened/elongated version of the potential match versus a clipped version of the potential match based on phonetic drift. In the present example, "hi HAL" is a near miss of 'hey HAL", but exhibits clipping (not slurring) in the first word ("hi" vs "hey") with a shorter vowel than the known phrase, whereas the near miss of "huh hull" exhibits vowel elongation in both words (e.g., "huh" vs "hey" and "hull" vs "HAL").

The assistant device may collect several utterances within a time window or search for additional signs before making a final determination that the patient is exhibiting slurred speech. Additionally, as different accents and vocal patterns affect what is considered "slurred speech", the assistant device may vary the analysis from patient to patient, and use various known phrases that are known to represent normal speech for the patient when identifying whether the received utterances include slurred speech. Accordingly, the assistant device can identify a normal vocal pattern for the patient for a known utterance and compare a received utterance against the known utterance to identify whether the differences between the two vocal patterns are due to natural variation in human speech or due to slurring characteristics imparted when suffering a stroke.

When the assistant device determines that the patient's speech is slurred and that the patient therefore may be non-responsive (e.g., unable to actively request assistance via spoken commands), method 600 proceeds to block 640 to determine whether additional signs point to the patient suffering a stroke. Otherwise, when the assistant device determines that the patient's speech is not slurred, or not slurred due to potential stroke, method 600 returns to block 610 to continue capturing audio from the environment.

At block 640, the assistant device determines if there are any additional signs that can point to or away from the patient currently suffering a stroke. In various embodiments, the assistant device may interface with additional sensors in the environment to receive additional signs of stroke. For example, a camera sensor with facial recognition may identify whether the patient's face is drooping or otherwise exhibiting partial facial paralysis (e.g., pointing to suffering a stroke). In some embodiments, the assistant device may access health records for the patient to identify another source for the slurred speech that would point away from suffering a stroke such as recent dental surgery or a medication prescribed to the patient with facial numbness or slurred speech as a side effect. Similarly, the health records may indicate whether the patient is at an increased risk for stroke (e.g., pointing to suffering a stroke), and should be identified as suffering a stroke as a precaution or prophylactic measure as early as possible. Additionally or alternatively to using the health records as an additional sign, when a patient is indicated as being at an elevated stroke risk, the assistant device may adjust the analysis thresholds used in method 600 to more readily generate an alert or determination that speech is slurred than for patients at a normal stroke risk.

When the additional signs point to the patient suffering a stroke, method 600 proceeds to block 660 to call for assistance on behalf of the patient. Otherwise, method 600 proceeds to block 650 to prompt for additional input to gauge whether the patient is suffering a stroke.

At block 650, the assistant device prompts for additional input to gauge whether the patient is suffering a stroke and is non-responsive. In various embodiments, the assistant device may activate various additional sensors in the environment to collect non-audio data (e.g., camera seniors to look for facial droop or facial expressions discontinuous to one side of a face of the patient) or connect to a remote repository for health records to receive medical information that can confirm or provide an alternative explanation for why a patient is slurring their speech. In some embodiments, the assistant device generates output audio directed to the patient to prompt responses to provide additional speech samples to analyze for slurring characteristics or alternative explanations for the slurring from the patient. For example, the assistant device may output "your speech sounds slurred, are you okay?" to the patient who may variously (intend to) respond with "what do you mean?" (e.g., providing an additional sample), "I just had a root canal" (e.g., providing an alternative explanation to stroke and an additional sample), or "I feel funny" (e.g., providing an positive support for stroke and an additional sample).

Additionally or alternatively, because muscle weakness (at least for half of the body) is another symptom of a stroke, the assistant device may use the audio evidence of the patient dropping an object or falling (e.g., as per method 400 discussed in relation to FIG. 4) within an analysis window (e.g., x minutes before or after detecting slurred speech) as additional input for making a determination that the patient is suffering a stroke.

Method 600 returns to block 610 from block 650 to capture additional audio from the environment.

At block 660, after determining that a patient is in distress and is non-responsive or that the patient approves of generating an alert, the assistant device calls for assistance for the patient. In various embodiments, the call for assistance is generated by a call system in communication with the assistant device that places a phone call or a text message to one or more specific personal devices for persons authorized to help the patient. Additionally or alternatively, the call system may transmit one alert as a multicast or broadcast to multiple personal devices (e.g., all devices for on-duty nurses in a healthcare facility) or to a community management device (e.g., a switchboard for a group home, an alert light in a hallway associated with a given room in a hospital, etc.).

Example Choking Scenarios

Figure 7:
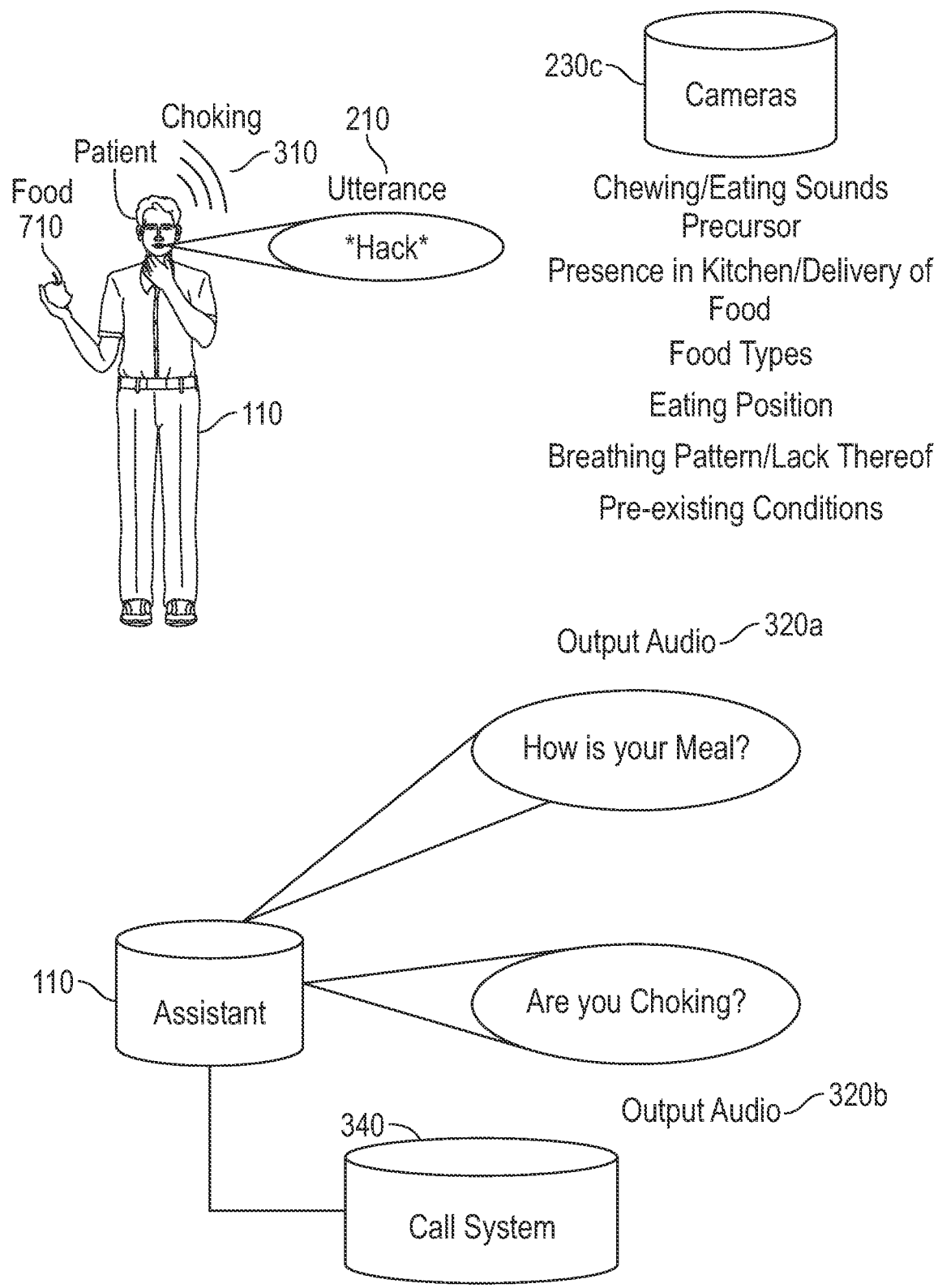
FIG. 7 illustrates an example scenario where an AI assistant device passively calls for assistance in response to identifying that a patient is choking, according to embodiments of the present disclosure.

FIG. 7 illustrates an example scenario where an AI assistant device 110 passively calls for assistance in response to identifying that a patient 120 is choking, according to embodiments of the present disclosure. Additionally or alternatively to monitoring a patient 120 via audio inputs from the patient 120 and the environment 700 for distress due to falls (e.g., as described in relation to FIGS. 3A-3D and 4), the present disclosure improves the functionality of the assistant device 110 to monitor a patient 120 for distress due to choking. Due to full or partial blockage of the airways when choking, the patient 120 may no longer be able to produce intelligible speech or otherwise actively call for assistance. Accordingly, the assistant device 110 may analyze utterances 210 generated by the patient 120 and environmental sounds 310 to determine when to generate an alert for a medical professional to diagnose and aid the patient 120.

As illustrated in FIG. 7, the patient 120 makes an utterance 210 of a hacking sound, indicative of a partially obstructed airway. Due to the patient's airway being obstructed, the patient 120 may be incapable of intelligible speech, even if having the presence of mind to attempt speech. In other examples, when the patient's airway is fully obstructed, the patient 120 may incapable of verbalizing at all, and no utterances 210 are captured by the assistant device 110.

Unlike other devices that remain inactive until a cue phrase is clearly received, an assistant device 110 operating according to the present disclosure may continuously monitor the environment 700 for human speech and environmental sounds 310 that would otherwise be discarded or ignored. Using these discarded sounds, an audio recognition engine provided by the assistant device 110 may look for sounds produced in the environment or by the patient 120 that match with choking sounds (including gasping or wheezing) or for a lack of response from the patient 120 to indicate when the patient 120 may be choking.

For example, an assistant device 110 may be set up to monitor a patient 120 at risk of choking by periodically issuing output audio to prompt the patient 120 to respond, such as the first audio output 320a of "how is your meal?". As illustrated, the utterance 210 that the patient 120 outputs after the first audio output 320a is posed is not responsive to the query, and the patient 120 may be assumed to be choking.

In various embodiments, an audio recognition engine provided locally on the assistant device 110 may monitor for various environmental sounds 310 associated with eating or choking to determine that a patient 120 is potentially choking in addition to or alternatively from monitoring the utterances 210 of the patient. For example, chewing sounds, crunching sounds, sounds of flatware and utensils interacting, etc., can all indicate eating behavior, and the cessation of these sounds in combination with choking sounds from the patient 120 may more strongly indicate choking than choking sounds while the easting sounds continue (e.g., a patient 120 clearing their throat vs. choking).

When the patient 120 is identified as being in distress as possibly choking, the assistant device 110 may generate various audio outputs 320 to prompt the patient 120 to provide an intelligible utterance 210 to counter-indicate the initial determination that the patient is choking. For example, a second utterance 210b of "are you choking" may be used to prompt the patient 120 to deny choking (e.g., "I was just chewing"), or confirm via lack of intelligible utterance 210 that the patient 120 is choking or otherwise in distress.

When the assistant device 110 detects choking sounds or fails to receive audio confirmation from the patient to a prompt to respond, the assistant device 110 may activate various supplemental sensors to further identify whether the patient is in distress. For example, a camera sensor 230 may be activated and the images provided to a facial recognition system (e.g., provided by remote computing resources 160) to identify whether the patient 120 has a facial expression associated with choking (e.g., eyes wide, mouth open in an "o") or a body position associated with chocking (e.g., one or both hands held to the throat).

Additionally or alternatively, the assistant device 110 may access health records 180 for the patient 120 to adjust the thresholds used to determine whether the utterances 210 and environmental sounds 310 are indicative of choking. For example, the health records 180 may indicate that a patient 120 is at an increased risk for choking, the confidence thresholds for choking may be adjusted downward to indicate choking more readily or earlier. In another example, when a patient 120 has been prescribed a liquid diet or other diet for easy chewing and swallowing to prevent choking, the assistant device 110 may raise the confidence thresholds for choking to avoid generating false positive alerts. In a further example, when a patient 120 has been prescribed a liquid diet or other diet for easy chewing and swallowing to prevent choking, and the assistant device 110 detects chewing sounds that should not be generated when eating food within an anti-choking diet, the assistant device may prophylactically generate an alert before other choking sounds are detected.

When, the assistant device 110 determines that the patient 120 is in distress and is non-responsive (despite potentially attempting to be responsive) due to choking, the assistant device 110 generates an alert that the patient 120 is in distress.

In various embodiments, the assistant device 110 transmits the alert to a call system 340 to propagate according to various transmission protocols to one or more personal devices 330 associated with authorized persons 130 to assist the patient 120. Example hardware as may be used in the call system 340 and the personal devices 330 can include a computing system 900 as is discussed in greater detail in FIG. 9. In some embodiments, the call system 340 is connected to a telephone network and pushes the alerts as one or more individual messages sent to a corresponding one or more personal devices 330 that are cellphones or pagers via text messages (e.g., via Short Message Service (SMS) or Multimedia Message Service (MMS)) or phone calls using a synthesized voice to alert the authorized persons 130 that the patient 120 is in distress. Additionally or alternatively, when the call system 340 is part of an alert system in a group home or medical facility, the call system 340 can transmit the alert via a broadcast message to be received by personal devices 330 associated with caretakers (as example authorized persons 130) in the group home or medical facility.

Figure 8:
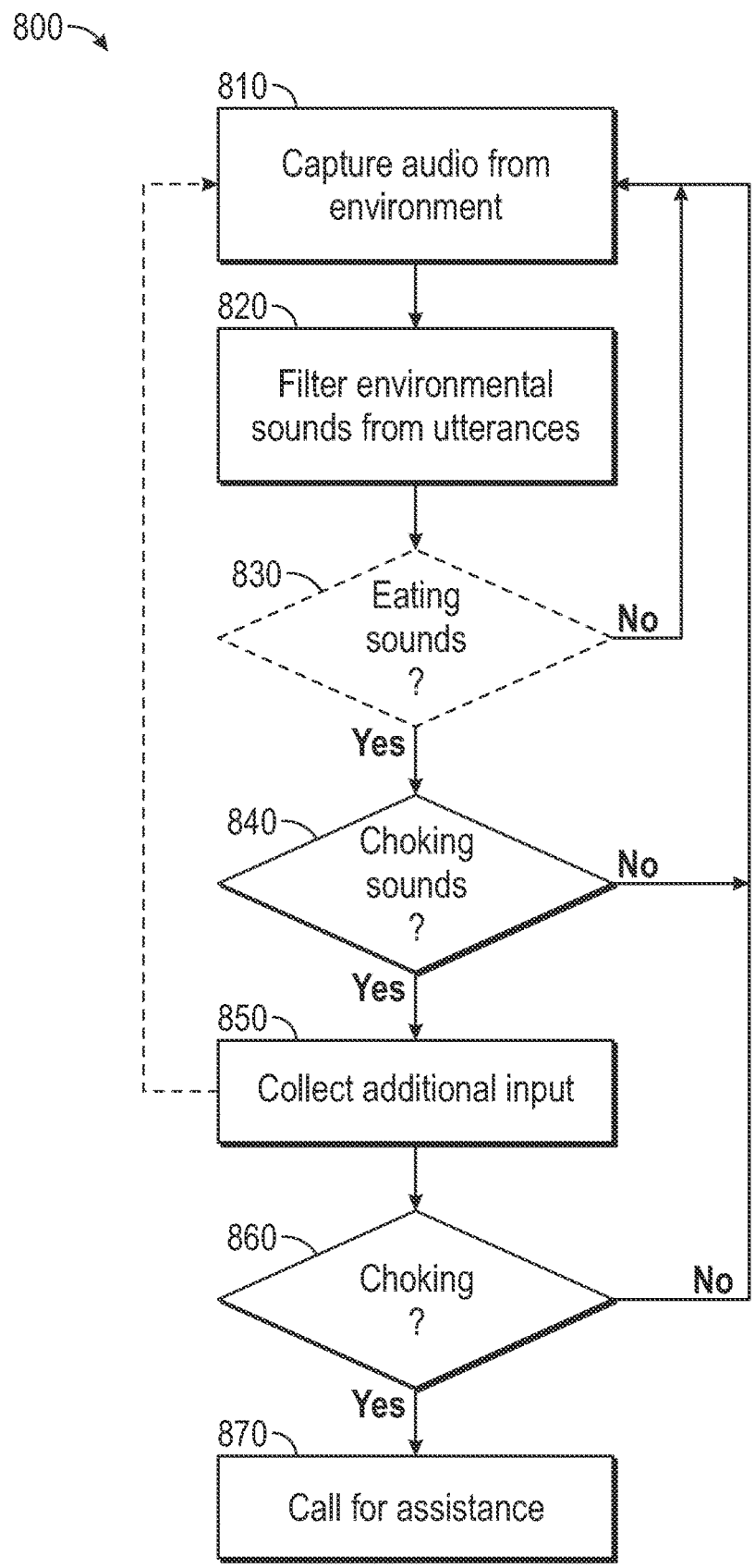
FIG. 8 is a flowchart of a method for passively identifying that a patient is choking and responding to the determination, according to embodiments of the present disclosure.

FIG. 8 is a flowchart of a method 800 for passively identifying and responding to a determination that a patient is choking, according to embodiments of the present disclosure. Method 800 begins at block 810, where the assistant device captures audio from the environment. In various embodiments, the assistant device may constantly capture audio from the environment as part of a "listening mode" used to wait for an activation cue to transition to an "active mode" to begin reacting to utterances with commands from a user to the assistant device. The audio received while in the "listening mode" may ordinarily be discarded by various assistant devices, but when analyzed according to the present disclosure, improve the functionality of the assistant device to passively identify when a patient is in distress and call for assistance on behalf of the user. In various embodiments, a user can enable (or disable) a "passive assistance mode" in the assistant device to perform (or not perform) method 800.

At block 820, a machine learning model provided by the assistant device filters the captured audio into two classes of sounds: environmental sounds and utterances (also referred to as speech sounds). The machine learning model may focus on certain frequency ranges based on demographic characteristics of the patient that affect voice frequency (e.g., age, gender, smoking habits, pulmonary or vocal medical conditions) to identify a fundamental frequency (e.g., between 85 and 255 Hz for adults) and harmonics (e.g., between 30 and 3500 Hz for adults) therein to identify speech sounds. Sounds not identified as related to speech, however, are retained for further analysis as environmental sounds. Frequency filtering is given as a non-limiting example for dividing captured audio into speech sounds and environmental sounds, but additional filtering is contemplated to identify environmental sounds within the frequency range of human speech and elements of human speech outside of the main ranges used for speech.

At block 830, an audio recognition engine provided by the assistant device (optionally), determines whether the environmental sounds include eating sounds. In various embodiments, the presence or absence of eating sounds that indicate that the patient is eating before a choking sound is detected is used as further evidence in support of a determination that a patient is choking. However, patients may choke on saliva or various objects (including food and beverages) that do not make (or were not observed to make) sounds when consumed. Accordingly, block 830 may be optionally omitted when performing method 800.

However, the various food items that are most likely to lead to difficulty in swallowing (and therefor lead to choking) are often accompanied by various environmental sounds when consumed. Accordingly, at block 830, the audio recognition engine may determine whether the environmental sounds include chewing sounds, slurping sounds, crunching sounds, the sounds of silverware or flatware being used, or the like to indicate that the patient is eating. Additionally, the environmental sounds can be used to identify various high-risk foods for choking are being consumed, as the soft foods prescribed for patients at an elevated risk of choking do not often crunch or otherwise produce pronounced chewing noises when consumed, may involve fewer utensils (or no utensils) to consume, and may more often result in slurping noises when consumed.

Accordingly, the various eating sounds may be used as a supplemental input for a choking determination when the eating sounds indicate high-risk foods are being consumed or that any foods are being consumed prior to detecting choking sounds.

At block 840, an audio recognition engine provided by the assistant device, determines whether the environmental sounds or speech sounds include choking sounds. Depending on the severity of a blockage to the patient's airway, the initial health of the patient, and where the blockage has occurred in the airway, the patient may make a variety of different sounds (variously described as hacking, wheezing, gasping, retching, coughing, etc.) or no speech sounds at all. Accordingly, the audio recognition engine may examine both the speech sounds generated by the patient and the environmental sounds, which may indicate that the patient is panicking or has passed out due to lack of air (e.g., pounding on a surface, dropping objects, falling, etc.). Accordingly, the audio recognition engine compares the various received audio to known audio clips to identify whether the patient is producing sounds (vocally or otherwise) that can indicate choking.

When no choking sounds are recognized from the audio by the audio recognition engine, method 800 returns to block 810 to continue capturing audio from the environment. When one or more choking sounds are recognized from the audio by the audio recognition engine, method 800 proceeds to block 850 to collect additional input to confirm the choking sounds are actually related to the patient choking, or if another explanation can be given for the sounds (e.g., a patient clearing their throat or coughing)

At block 850, the assistant device collects additional input to gauge whether the patient is choking and is non-responsive. In various embodiments, the assistant device may activate various additional sensors in the environment to collect non-audio data (e.g., camera seniors to look for food in the environment or a facial expression or body position indicative of choking). For example, when the camera sensor indicates that food items are in the environment (and in proximity to the patient) or that the body position of the patient is associated with increased risk of choking (e.g., laying down or reclining versus standing or sitting upright), these visual data may be used to supplement an audio determination that the patient is choking. Other non-audio sensors may include breathing rate monitors, airflow monitors, blood oxygenation monitors, heart monitors (e.g., tachycardia accompanying panic when choking), and the like.

In some embodiments, the assistant device may connect to a remote repository for health records to receive medical information that can confirm or provide an alternative explanation for why a patient may be choking. For example, when the health records indicate that the patient has an elevated risk for choking (e.g., after throat or dental surgery), the health records can confirm that the patient is choking. Additionally or alternatively to using the health records as an additional sign, when a patient is indicated as being at an elevated choking risk, the assistant device may adjust the analysis thresholds used in method 800 to more readily generate an alert or determination that the patient is choking than patients at a normal choking risk.

Additionally, the visual identification (e.g., by a food recognition system associated with the camera sensor) or a meal receipt included in health information (e.g., an order placed to a kitchen associated with a group home or hospital) can identify whether any food items in the environment or provided to the patient or otherwise in the environment have a choking risk above a safety threshold for the patient based on health records for the patient.

Additionally or alternatively, because panic and lack of oxygen are additional symptom of choking, the assistant device may use the audio evidence of the patient dropping an object or falling (e.g., as per method 400 discussed in relation to FIG. 4) as additional input for making a determination that the patient is choking.

In some embodiments, the assistant device generates various output audio to prompt the patient to provide an intelligible utterance to counter-indicate the choking sounds identified per block 840. For example, the assistant device may ask the patient "are you choking?", and the patient may respond "I was just clearing my throat" to deny choking or confirm (via lack of intelligible response or additional wheezing/gasping/retching) that the patient is choking or otherwise in distress. When collecting additional input includes generating an audio prompt for the patient to respond to, method 800 may return to block 810 to capture the potential response, or may wait a predefined amount of time before determining that no response has been received, which is indicative of the patient choking.

At block 860, the audio recognition engine determines whether the patient is choking and is therefore non-responsive and an alert should be generated on behalf of the patient. When the choking sounds and supporting input (including environmental sounds of eating or panicking while choking, visual indications of choking or elevated risk for choking, and health records for risk of choking) indicate that the patient is likely choking, method 800 proceeds to block 870. Otherwise, method 800 returns to block 810 to continue capturing the audio from the environment.

At block 870, after determining that a patient is in distress and is non-responsive (or that the patient approves of generating an alert), the assistant device calls for assistance for the patient. In various embodiments, the call for assistance is generated by a call system in communication with the assistant device that places a phone call or a text message to one or more specific personal devices for persons authorized to help the patient. Additionally or alternatively, the call system may transmit one alert as a multicast or broadcast to multiple personal devices (e.g., all devices for on-duty nurses in a healthcare facility) or to a community management device (e.g., a switchboard for a group home, an alert light in a hallway associated with a given room in a hospital, etc.).

Example Computing Hardware

Figure 9:
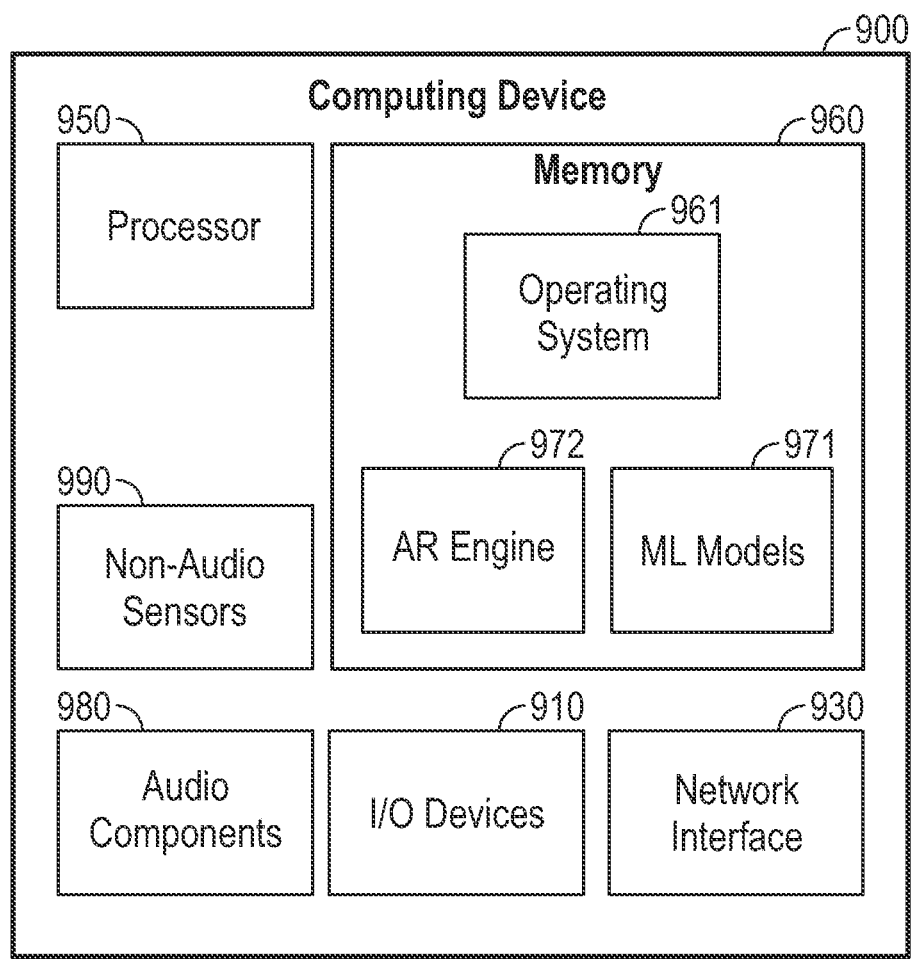
FIG. 9 illustrates a computing system, according to embodiments of the present disclosure.

FIG. 9 illustrates a computing system 900, which may be an assistant device 110, a personal device 330 (e.g., a computer, a laptop, a tablet, a smartphone, etc.), or any other computing device described in the present disclosure. As shown, the computing system 900 includes, without limitation, a processor 950 (e.g., a central processing unit (CPU)), a network interface 930, and memory 960. The computing system 900 may also include an input/output (I/O) device interface connecting I/O devices 910 (e.g., keyboard, display and mouse devices) to the computing system 900.

The processor 950 retrieves and executes programming instructions stored in the memory 960. Similarly, the processor 950 stores and retrieves application data residing in the memory 960. An interconnect can facility transmission, such as of programming instructions and application data, between the processor 950, I/O devices 910 network interface 930, and memory 960. The processor 950 is included to be representative of a single processor, multiple processors, a single processor having multiple processing cores, and the like. And the memory 960 is generally included to be representative of a random-access memory. The memory 960 can also be a disk drive storage device. Although shown as a single unit, the memory 960 may be a combination of fixed and/or removable storage devices, such as magnetic disk drives, flash drives, removable memory cards or optical storage, network attached storage (NAS), or a storage area-network (SAN). The memory 960 may include both local storage devices and remote storage devices accessible via the network interface 930. One or more machine learning models 971 may be are maintained in the memory 960 to provide localized portion of an AI assistant via the computing system 900. Additionally, one or more AR engines 972 may be maintained in the memory 960 to match identified audio to known events occurring in an environment where the computing system 900 is located.

Further, the computing system 900 is included to be representative of a physical computing system as well as virtual machine instances hosted on a set of underlying physical computing systems. Further still, although shown as a single computing system, one of ordinary skill in the art will recognize that the components of the computing system 900 shown in FIG. 9 may be distributed across multiple computing systems connected by a data communications network.

As shown, the memory 960 includes an operating system 961. The operating system 961 may facilitate receiving input from and providing output to various audio components 980 and non-audio sensors 990. In various embodiments, the audio components 980 include one or more microphones (including directional microphone arrays) to monitor the environment for various audio including human speech and non-speech sounds, and one or more speakers to provide simulated human speech to interact with persons in the environment. The non-audio sensors 990 may include sensors operated by one or more different computing systems 900, such as, for example, presence sensors, motion sensors, cameras, pressure or weight sensors, light sensors, humidity sensors, temperature sensors, and the like, which may be provided as separate devices in communication with an assistant device 110, or a managed constellation of sensors (e.g., as part of a home security system in communication with an assistant device 110). Although illustrated as external to the computing system 900, and connected via an I/O interface, in various embodiments, some or all of the audio components 980 and non-audio sensors 990 may be connected to the computing system 900 via the network interface 930, or incorporated in the computing system 900.

Additional Considerations

The preceding description is provided to enable any person skilled in the art to practice the various embodiments described herein. The examples discussed herein are not limiting of the scope, applicability, or embodiments set forth in the claims. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, the word "exemplary" means "serving as an example, instance, or illustration." Any aspect described herein as "exemplary" is not necessarily to be construed as preferred or advantageous over other aspects.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a c c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

The following clauses describe various embodiments of the present disclosure.

Clause 1: A method comprising capturing, via an Artificial Intelligence (AI) assistant device, audio from an environment; filtering, via a machine learning model provided by the AI assistant device, an environmental sound from utterances in the audio; determining, via an audio recognition engine provided by the AI assistant device and based on the environmental sound, that a patient is in distress and is non-responsive; and generating an alert via a call system in communication with the AI assistant device.

Clause 2: In addition to the method of clause 1, wherein the call system transmits the alert via a phone network to a personal device associated with a caretaker for the patient as at least one of: a text message; or a phone call using a synthesized voice.

Clause 3: In addition to the method of clauses 1 or 2, wherein the call system is part of an alert system in a group home or medical facility, wherein the call system transmits the alert via a broadcast message to personal devices associated with caretakers in the group home or medical facility.

Clause 4: In addition to the method of clauses 1, 2, or 3, wherein the audio recognition engine determines that the patient is in distress and is non-responsive based on the environmental sound matching a fall sound and a lack of utterances from the patient within a time window from when the environmental sound was received.

Clause 5: In addition to the method of clauses 1, 2, 3, or 4, wherein the audio recognition engine determines that the patient is in distress and is non-responsive based on the environmental sound matching a fall sound and a biometric monitor associated with the patient and in communication with the AI assistant device indicating a vital sign outside of a healthy range Clause 6: In addition to the method of clauses 1, 2, 3, 4, or 5, wherein determining that the patient is in distress and is non-responsive comprises: matching the environmental sound to a fall sound; and receiving, from a motion sensor associated with the environment, an indication of a lack of movement in the environment within a time window from when the environmental sound was received, wherein the motion sensor is in communication with the AI assistant device.

Clause 7: In addition to the method of clauses 1, 2, 3, 4, 5, or 6, wherein the audio recognition engine determines that the patient is in distress and is non-responsive based on recognizing speech slurring in the utterances that are attributable to the patient Clause 8: In addition to the method of clause 1, 2, 3, 4, 5, 6, or 7, wherein the audio recognition engine determines that the patient is in distress and is non-responsive based on recognizing choking sounds from the environmental sound after recognizing eating sounds from the environment.

Clause 9: In addition to the method of clause 8, further comprising: supplementing the audio recognition engine to determine that the patient is in distress and is non-responsive via a camera sensor identifying a body position of the patient associated with choking.

Clause 10: In addition to the method of clauses 8 or 9, further comprising: supplementing the audio recognition engine to determine that the patient is in distress and is non-responsive via a camera sensor identifying a food item in the environment associated with a choking risk above a safety threshold for the patient based on health records for the patient.

Clause 11: A method, comprising: capturing, via an Artificial Intelligence (AI) assistant device, audio from an environment; identifying utterances in the audio using the AI assistant device; determining, via an audio recognition engine provided by the AI assistant device, that the utterances indicate that a patient has slurred speech and is non-responsive; and generating an alert via a call system in communication with the AI assistant device.

Clause 12: In addition to the method of clause 11, wherein the audio recognition engine is a machine learning model trained to recognize stroke symptoms based on: identifying a normal vocal pattern for the patient for a known utterance; and comparing a received utterance against the known utterance for slurring characteristics in a received vocal pattern in the received utterance.

Clause 13: In addition to the method of clauses 11 or 12, further comprising, before generating the alert: identifying via a camera sensor associated with a facial recognition system that the patient is exhibiting at least one of: facial droop; or facial expressions discontinuous to one side of a face of the patient; and indicating in the alert that the patient is experiencing a stroke.

Clause 14: In addition to the method of clauses 11, 12, or 13, further comprising, before generating the alert: identifying from environmental sounds, via the audio recognition engine, that an object has fallen in the environment within an analysis window of determining that patient has slurred speech and is non-responsive; and indicating in the alert that the patient is experiencing a stroke.

Clause 15: In addition to the method of clauses 11, 12, 13, or 14, further comprising, before generating the alert: identifying from an electronic health record a stroke risk for the patient; and adjusting a sensitivity of a confidence threshold for when to generate the alert based on the stroke risk.

Clause 16: A method, comprising: capturing, via an Artificial Intelligence (AI) assistant device, audio from an environment; identifying utterances in the audio using the AI assistant device; determining, via an audio recognition engine provided by the AI assistant device, that the utterances captured indicate that a patient is choking; and generating an alert via a call system in communication with the AI assistant device.

Clause 17: In addition to the method of clause 16, further comprising: determining, via the audio recognition engine, before determining that the utterances indicates that the patient is choking, that environmental sounds detected by the AI assistant device indicate that the patient is eating.

Clause 18: In addition to the method of clause 17, further comprising: supplementing the audio recognition engine to determine one or both of that the patient is eating or that the patient is choking via a camera sensor identifying food items in the environment and a body position of the patient.

Clause 19: In addition to the method of clause 18, wherein the camera sensor identifies the food items in the environment as having a choking risk above a safety threshold for the patient based on health records for the patient.

Clause 20: In addition to the method of clauses 16, 17, 18, or 19, wherein the audio recognition engine is a machine learning model trained to categorize environmental sounds captured by the AI assistant device indicative of: a person falling; eating various food items; flatware or utensils being used by the patient; gasping or wheezing; and pounding on a surface.

What is claimed is:

1. A method, comprising:
   capturing, via an Artificial Intelligence (AI) assistant device, audio from an environment;
   filtering, via a machine learning model provided by the AI assistant device, an environmental sound from utterances in the audio;
   determining, via an audio recognition engine provided by the AI assistant device and based on the environmental sound, that a patient is in distress and is non-responsive based on recognizing choking sounds from the environmental sound after recognizing eating sounds from the environment; and
   generating an alert via a call system in communication with the AI assistant device.

2. The method of claim 1, wherein the call system transmits the alert via a phone network to a personal device associated with a caretaker for the patient as at least one of:
   a text message; or
   a phone call using a synthesized voice.

3. The method of claim 1, wherein the call system is part of an alert system in a group home or medical facility, wherein the call system transmits the alert via a broadcast message to personal devices associated with caretakers in the group home or medical facility.

4. The method of claim 1, further comprising:
   supplementing the audio recognition engine to determine that the patient is in distress and is non-responsive via a camera sensor identifying a body position of the patient associated with choking.

5. The method of claim 1, further comprising:
   supplementing the audio recognition engine to determine that the patient is in distress and is non-responsive via a camera sensor identifying a food item in the environment associated with a choking risk above a safety threshold for the patient based on health records for the patient.

6. A method, comprising:
   capturing, via an Artificial Intelligence (AI) assistant device, audio from an environment;
   identifying utterances in the audio using the AI assistant device;
   determining, via an audio recognition engine provided by the AI assistant device, that the utterances captured indicate that a patient is choking;
   determining, via the audio recognition engine, before determining that the utterances indicates that the patient is choking, that environmental sounds detected by the AI assistant device indicate that the patient is eating; and
   generating an alert via a call system in communication with the AI assistant device.

7. The method of claim 6, further comprising:
   supplementing the audio recognition engine to determine one or both of that the patient is eating or that the patient is choking via a camera sensor identifying food items in the environment and a body position of the patient.

8. The method of claim 7, wherein the camera sensor identifies the food items in the environment as having a choking risk above a safety threshold for the patient based on health records for the patient.

9. The method of claim 6, wherein the audio recognition engine is a machine learning model trained to categorize environmental sounds captured by the AI assistant device indicative of:

a person falling;
eating various food items;
flatware or utensils being used by the patient;
gasping or wheezing; and
pounding on a surface.

10. An Artificial Intelligence (AI) assistant device, comprising:
a microphone configured to capture audio from an environment;
a machine learning model configured to filter an environmental sound from utterances in the audio;
an audio recognition engine configured to:
determine, based on the environmental sound, that a patient is in distress and is non-responsive based on recognizing choking sounds from the environmental sound after recognizing eating sounds from the environment; and
transmit an alert to a call system in communication with the AI assistant device.

11. A method, comprising:
capturing, via an Artificial Intelligence (AI) assistant device, audio from an environment;
filtering, via a machine learning model provided by the AI assistant device, an environmental sound from utterances in the audio;
determining, via an audio recognition engine provided by the AI assistant device, that a patient is in distress and is non-responsive based on the environmental sound matching a fall sound and a biometric sensor in communication with the AI assistant device and configured to obtain non-voice biometric data indicating a vital sign of the patient is outside of a healthy range; and
generating an alert via a call system in communication with the AI assistant device.

12. The method of claim 11, wherein the biometric sensor comprises a heart rate monitor, and wherein the vital sign comprises a heart rate of the patient.

13. The method of claim 11, wherein the biometric sensor comprises a breath rate sensor, and wherein the vital sign comprises a breath rate of the patient.

14. The method of claim 11, wherein determining the patient is in distress and is non-responsive based on image data from one or cameras indicating the patient is immobile.

15. The method of claim 14, wherein the image data further indicates a presence of a body fluid by the patient.

* * * * *